United States Patent
Hershoff et al.

(10) Patent No.: US 10,765,553 B2
(45) Date of Patent: Sep. 8, 2020

(54) CONTACT LENS MANIPULATOR WITH SUCTION CUP AND SAFETY RELEASE MECHANISM

(71) Applicant: Craig L. Hershoff, Sunny Isles Beach, FL (US)

(72) Inventors: Craig L. Hershoff, Sunny Isles Beach, FL (US); Andres Bernal, Sunny Isles Beach, FL (US)

(73) Assignee: Craig L. Hershoff, Sunny Isles Beach, FL (US)

( * ) Notice: Subject to any disclaimer, the term of this patent is extended or adjusted under 35 U.S.C. 154(b) by 0 days.

(21) Appl. No.: 16/329,380

(22) PCT Filed: Aug. 29, 2017

(86) PCT No.: PCT/US2017/049067
§ 371 (c)(1),
(2) Date: Feb. 28, 2019

(87) PCT Pub. No.: WO2018/044861
PCT Pub. Date: Mar. 8, 2018

(65) Prior Publication Data
US 2019/0216644 A1    Jul. 18, 2019

Related U.S. Application Data

(60) Provisional application No. 62/537,507, filed on Jul. 27, 2017, provisional application No. 62/450,789, (Continued)

(51) Int. Cl.
*A61F 9/00*    (2006.01)
*B25J 15/06*    (2006.01)

(52) U.S. Cl.
CPC ........... *A61F 9/0061* (2013.01); *B25J 15/065* (2013.01); *B25J 15/0683* (2013.01)

(58) Field of Classification Search
CPC ... A61F 9/0061; B25J 15/065; B25J 15/0683; B25B 11/007
(Continued)

(56) References Cited

U.S. PATENT DOCUMENTS

| | | |
|---|---|---|
| 3,934,914 A | 1/1976 | Carruthers |
| 4,037,866 A | 7/1977 | Price |

(Continued)

FOREIGN PATENT DOCUMENTS

WO    WO 1993-004648    3/1993

OTHER PUBLICATIONS

The DMV® Ultra™ product information [online, webpage, retrieved Aug. 16, 2017 from http://www.dmvcorp.com/gas_permeable_products.htm, pp. 1-2.

*Primary Examiner* — Dean J Kramer
(74) *Attorney, Agent, or Firm* — Saliwanchik, Lloyd & Eisenschenk

(57) ABSTRACT

A lens manipulator that includes an over-sleeve with a suction cup and lumen therethrough that forms a pore in the suction cup and a rod opening at the opposite end for receiving an adjustment rod. Adjustment of the length of the adjustment rod in the lumen controls the amount of suction force generated under the suction cup against a contact lens. Removal of the adjustment rod from the lumen eliminates the suction force and acts as a safety release against excessive pull force on an eye when removing a contact lens.

24 Claims, 18 Drawing Sheets

Related U.S. Application Data filed on Jan. 26, 2017, provisional application No. 62/381,007, filed on Aug. 29, 2016.

(58) Field of Classification Search
USPC .......................................................... 294/1.2
See application file for complete search history.

(56) References Cited

U.S. PATENT DOCUMENTS

| | | | |
|---|---|---|---|
| 4,071,272 A | | 1/1978 | Drdlik |
| 4,113,297 A | * | 9/1978 | Quinn .................. A61F 9/0061 |
| | | | 294/1.2 |
| 4,123,098 A | * | 10/1978 | Shoup .................. A61F 9/0061 |
| | | | 294/1.2 |
| 4,201,408 A | | 5/1980 | Tressel |
| 4,238,134 A | | 12/1980 | Cointment |
| 4,286,815 A | | 9/1981 | Clark |
| 4,378,126 A | | 3/1983 | Procenko |
| 4,565,396 A | | 1/1986 | Larimer |
| 5,069,494 A | * | 12/1991 | Reinson ............... A45C 11/005 |
| | | | 206/5.1 |
| 5,941,583 A | | 8/1999 | Raimondi |
| 6,398,277 B1 | * | 6/2002 | McDonald ............ A61F 9/0061 |
| | | | 294/1.2 |
| 7,163,245 B2 | | 1/2007 | Wallock et al. |
| 7,168,746 B2 | | 1/2007 | Py |
| 2015/0265467 A1 | | 9/2015 | Hershoff |
| 2017/0105872 A1 | | 4/2017 | Fama |

\* cited by examiner

CONTACT LENS MANIPULATOR WITH SUCTION CUP AND SAFETY RELEASE MECHANISM

CROSS-REFERENCE TO RELATED APPLICATIONS

This application is the U.S. national stage application of International patent application No. PCT/US2017/049067, filed Aug. 29, 2017, which claims the benefit of U.S. Provisional Application Ser. No. 62/537,507, filed Jul. 27, 2017, U.S. Provisional Application Ser. No. 62/450,789, filed Jan. 26, 2017, and U.S. Provisional Application Ser. No. 62/381,007, filed Aug. 29, 2016, the disclosures of which are hereby incorporated by reference in their entireties, including all Figures, tables and drawings.

BACKGROUND OF INVENTION

Contact lens wearers usually insert and remove their contact lenses manually. With Rigid Gas Permeable (RGP) and the new hybrid contact lenses this task can be more complicated. Hybrid lenses are designed to correct atypical vision problems and have irregular thicknesses, often a rigid central zone and softer peripheral zone. These types of specialized contact lenses are often larger in diameter and can form a stronger adherence to the eye surface, which can make them difficult to remove. Inserting and removing contact lenses can have other ergonomic limitations, given that it is a maneuver that typically requires manual dexterity, coordination, and stability. People for whom inserting and removing RGP and hybrid contact lenses with their fingers can be a difficult task includes seniors, children, superior-limb handicapped individuals, those with long fingernails, or anyone lacking the necessary manual dexterity or stability.

A variety of lens manipulators with suction cups have been developed to manipulate specialized contact lenses, but many are not equally effective for both insertion and removal of a contact lens. If the suction cup of the lens manipulator can provide sufficient suction on contact with the contact lens to facilitate removal, that same force may not release the contact lens when the suction cup is retracted. Likewise, if suction or adherence is sufficient to facilitate insertion and easy release, then the suction cup may not exert sufficient suction to be effective for removal.

Some lens manipulators utilize suction cups that rely on "passive" vacuum force, wherein the vacuum force in the cup depends upon the volume of air displacement under the concave surface of the suction cup. Air displacement can be accomplished by either pressing the suction cup onto a surface to compress the suction cup, or by pressing/releasing a flexible or pliant bulb attached to the suction cup. Either method results in a decrease in pressure under the suction cup. These techniques, usually manually controlled, may not provide sufficient control over the vacuum force that the cup can exert on the contact lens and the eye. Thus, the amount of pressure under the suction cup cannot be precisely or consistently regulated. Further, if the contact lens is stuck to the eye and cannot be removed normally, it can be difficult to disengage the already attached suction cup from the contact lens.

Other lens manipulators for contact lens insertion and extraction can provide "active" vacuum or positive pressure with the use of a pump, such as, for example, the CLIARA device disclosed in U.S. Published Application No. 2015/0265467. These types of devices can require specific configurations of suction cups to facilitate the formation and release of vacuum force within the cup.

Surface tension, Van der Waal's forces, hydrophilic/hydrophobic interactions, and other factors can affect the surface interaction between the contact lens and the suction cup. Certain materials, surface finishes, textures, additives or coatings, and other substances can make the suction cup surface "sticky," causing it to adhere to the lens surface, independent of the vacuum pressure. A suction cup with a "sticky" surface can be beneficial for contact lens extraction, but inhibit contact lens insertion by not releasing the lens once engaged with the eye. The opposite can also be true, where a non-sticky surface can be beneficial for insertion, but can inhibit extraction.

There is a need for a suction cup that addresses the limitations of previously known suction cups on such devices, with regard to insertion and removal of contact lenses. Ideally, such a suction cup can be used with a lens manipulator that can aid in inserting and removing contact lenses with more control over the amount of suction force. Such a device can, ideally, reduce the amount of manual dexterity and coordination required to remove and insert specialized contact lenses, and inhibits undesirable contact with the cornea or sclera of the eye. It can also be advantageous if the device can be released by a user through activation of a quick-release mechanism or to release the contact lens automatically if excessive extraction force is applied to the contact lens.

BRIEF SUMMARY

In accordance with the invention, the problem of handling a contact lens for depositing and extracting from the surface of an eye is solved by a lens manipulator with a suction cup in which the suction force can be accurately adjusted or customized to an individual. The advantageous ability to adjust the amount of suction force exerted by the suction cup of the lens manipulator can facilitate release of the contact lens by inhibiting the suction cup from remaining attached to the contact lens during an insertion procedure. The lens manipulator can also have the ability to fully release the suction force exerted by the suction cup, often during an extraction procedure, if excessive pulling force is applied to the suction cup. This feature enables the suction cup to safely release from a contact lens that is too firmly attached to the eye, mitigating the risk of injury. The lens manipulator can also be released voluntarily by the user at any time if desired.

Suction cups typically have a conical, semi-circular, or similarly concave shape and are made of a malleable material that can flatten when the concave side is pushed towards an object and usually biased to return to the original shape. The suction force generated by a suction cup is dependent upon both the difference in air pressure between the outside and inside of the cup and the surface area under the cup. If either one of these factors is increased or decreased, it can affect the amount of suction force produced by the suction cup.

When the suction cup engages with the contact lens before it is deposited on the eye, the formation of even a small $_{[O1]}$attraction force between the suction cup and the contact lens can make it difficult for the contact lens to disengage from the suction cup and remain on the eye. Also disclosed herein are embodiments of a suction cup with a discontinuous peripheral edge. The discontinuous peripheral edge can support the contact lens while preventing the formation of a continuous seal with the lens surface. This minimizes the formation of a suction force that would inhibit a contact lens to be inserted on the eye. When an intentional force is applied, such as when a contact lens is to be extracted, the discontinuous peripheral edge can flattened or radially deflected as the suction cup is pushed onto the contact lens, so that a continuous edge 80 on the suction cup is exposed or made available to make sealing contact with the contact lens, allowing formation of vacuum under the suction cup. In one embodiment, the suction cup can be attached to a stem that can be used to manipulate the suction cup.

Some contact lenses can be more easily extracted when the extraction force is applied eccentrically. With eccentric extraction the suction cup engages the contact lens surface off-center. Engaging the contact lens off-center can necessitate that a suction cup attached to a stem be able to bend, rotate, or otherwise adjust position relative to the stem, so that the leading edge can make full contact with the lens. Embodiments of the subject invention provide a flexible stem that allows the suction cup to be engaged in an eccentric manner with the contact lens.

Deposition of a contact lens on the cornea typically does not require the application of force to the cornea. The fluid reservoir or concave surface of the contact lens can be filled with an appropriate fluid, such as sterile saline solution, which can provide sufficient surface tension and adhesion to pull the contact lens onto the corneal surface when the contact lens is brought into proximity with the eye. Extraction of a contact lens can be problematic if there is stronger than usual attraction forces between the eye and the contact lens. If a suction cup applied to the convex surface of the contact lens forms stronger than usual or stronger than necessary attractive forces, a suction cup may not pull off or disengage from the contact lens.

Embodiments of the subject invention provide an advantageous safety mechanism by which the suction cup can be easily disengaged from the convex surface of the contact lens with minimal or no application of pull force on the eye. The safety mechanism can release the vacuum between the suction cup and a contact lens, causing the suction cup to disengage from the surface of the contact lens. The application of medicines, drugs, pharmaceutical compositions, and other substances or materials to the eye can also be problematic. Embodiments of the subject invention can be used as applicators for such substances and medicaments. The suction cup can be filed with the substance and applied to the eye. Alternatively, a contact lens can be employed as an intermediate applicator between the suction cup and the eye.

In one general embodiment, a lens manipulator has an over-sleeve with a suction cup at the proximal end of a stem 210 and a lumen through at least some portion of, or the full, longitudinal length. At the proximal end, the lumen terminates in a pore that opens into the suction cup. The distal end of the lumen can be placed over an adjustment rod or, alternatively, a plug with a nipple. The combination of the lumen and the adjustment rod or plug therein provides control over the amount of suction strength that can be formed under the suction cup. By moving the adjustment rod into or out of the lumen, the air pressure that can be generated under the suction cup can be increased or decreased, as needed. Advantageously, if the rod or plug is removed from the lumen, such that ambient air can intrude through the lumen, the force under the suction cup is entirely released. This can inhibit excessive or damaging pull force being applied to a contact lens that may be stuck to the eye. The over-sleeve and adjustment rod can be configured so that the rod is pulled from the lumen if a predetermined maximum amount of pulling force is applied. Further embodiments can include a cuff that further aids in providing friction against the over-sleeve to control movement of the rod in the lumen.

When installing a contact lens on the eye, the suction cup can be directed upwards and a contact lens can be placed on the suction cup, without the application of force that would cause the suction force to stick to the contact lens. The concavity of the contact lens can then be filled with saline or other contact lens solution or medicines or drugs, as mentioned above. Bending forward to bring the eye into proximity with the suction cup causes the eye surface to contact the lens solution, thereby pulling the contact lens away from the suction cup and onto the eye surface.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF DRAWINGS

In order that a more precise understanding of the above recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not therefore to be considered as limiting in scope, the invention will be described and explained with additional specificity and detail through the use of the accompanying drawings in which:

FIG. 5A is an embodiment of a completely assembled lens manipulator. FIG. 5B is an embodiment of a lens manipulator without the over-sleeve. FIG. 5C is an embodiment of a lens manipulator without the suction cup.

FIG. 18B illustrates how the radial ribs can cause an uneven pulling force on the suction cup forming a pucker or fold in the contact to release suction.

FIG. 19A shows a contact lens on a discontinuous peripheral edge and FIG. 19B shows the discontinuous peripheral edge deflected and the contact lens in contact with the continuous edge.

DETAILED DISCLOSURE

Figure 1:
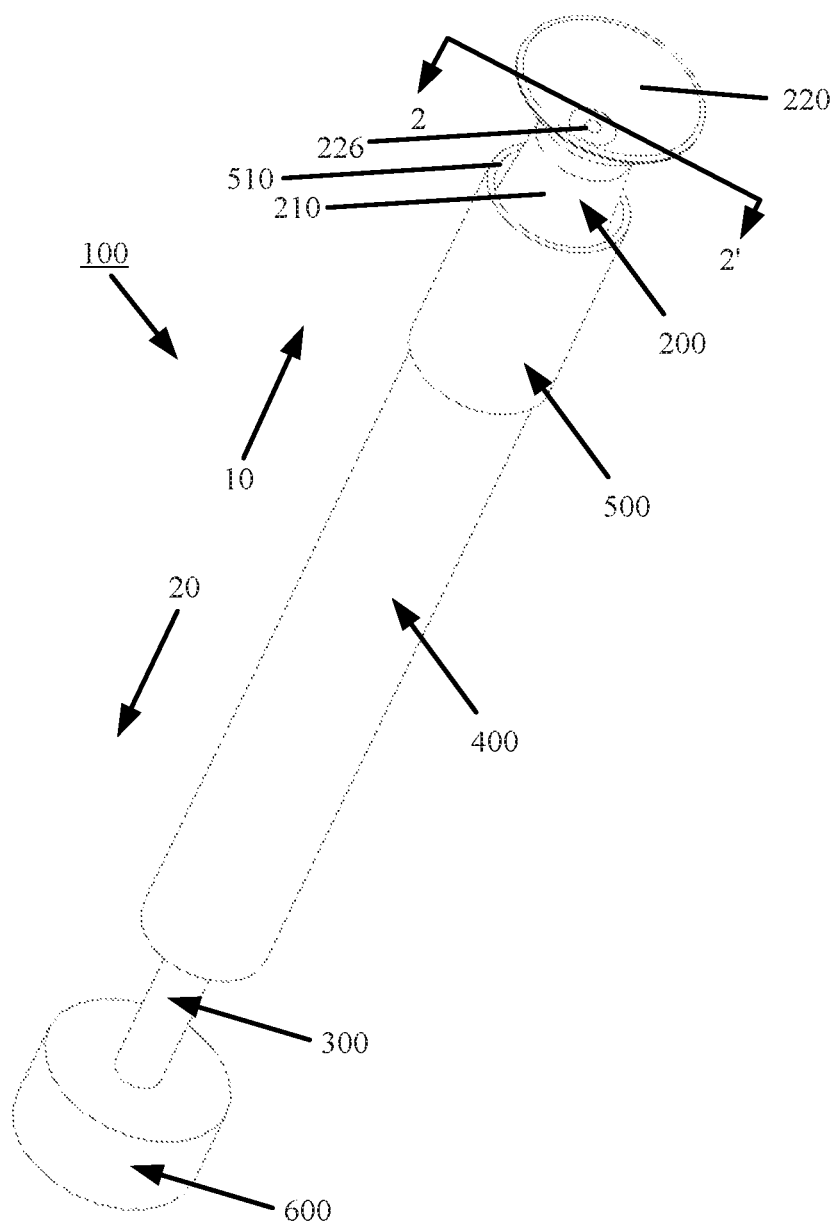
FIG. 1 is an illustration of a lens manipulator, according to an embodiment of the subject invention.

The subject invention pertains to devices and methods for inserting and removing a contact lens from the surface of an eye. More specifically, the subject invention provides one or more embodiments of a lens manipulator for use in handling Rigid Gas Permeable (RGP) and Hybrid contact lenses for insertion or removal from the surface of an eye. Lens manipulator embodiments of the subject invention employ a suction cup to hold a contact lens. Advantageously, the amount of suction force exerted onto a contact lens by a lens manipulator of the subject invention can be adjusted. If the maximum pulling force of the lens manipulator is insufficient to remove a contact lens, a safety release mechanism can inhibit the application of excessive pulling force on the eye when extracting a contact lens. The safety release mechanism can be activated automatically during use or, if necessary, intentionally by a user to release the suction cup from a contact lens. While embodiments of the subject invention are particularly useful with Rigid Gas Permeable (RGP) and newer hybrid lenses, a person with skill in the art will recognize embodiments that can be utilized with other types of contact lenses.

The terms "contact" and "contact lens" are used herein for literary convenience. The devices and methods of the subject invention can be suited for use with RGP and with hybrid contact lenses with a rigid or semi-rigid center portion and a softer, more pliable outer ring portion. This does not preclude the embodiments herein, or variations thereof, being useful for other types of contact lenses.

The term "pull force" is used herein to refer to the force applied to a suction cup against any adherent force formed between said suction cup, and a surface, such as a contact lens. A pull force can be applied in a direction away from the concavity of the suction cup or away from the surface to which the suction cup is attached. For example, as described herein, a pull force is used to remove a contact lens from an eye. Also as used herein, the term "maximum pull force" is the force necessary to remove an over-sleeve from the end of an adjustment rod.

As used herein, the terms "longitude" or "longitudinal length" refer to the longitudinal measurement or the distance extending along the long axis. For example, the longitude or longitudinal length of a lens manipulator is the distance or direction between the proximal end to the distal end.

Finally, reference is made throughout the application to the "proximal end" or "proximal direction" and "distal end" or "distal direction." As used herein, the proximal end or proximal direction is that end that approaches or comes nearest to the eye. For example, the suction cup is at the proximal end of the lens manipulator. Conversely, the distal end or distal direction of the device is that end which approaches or is nearest to the hand during use or furthest from the eye. For example, ergonomic structures, such as a handle, for holding the lens manipulator with the fingers or hand can be located at the distal end of the lens manipulator. As further example, the rod opening can be at the distal end of an over-sleeve.

It is to be understood that the figures and descriptions of embodiments of the present invention have been simplified to illustrate elements that are relevant for a clear understanding of the invention, while eliminating, for purposes of clarity, other elements that may be well known. Those of ordinary skill in the art will recognize that other elements may be desirable and/or required in order to implement the present invention. However, because such elements are well known in the art, and because they do not facilitate a better understanding of the present invention, a discussion of such elements is not provided herein.

The present invention is more particularly described in the following examples that are intended to be illustrative only because numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached Figures, which show certain embodiments of the subject invention, it can be seen that the subject invention, in general, comprises a lens manipulator 100 that includes an elongated over-sleeve 200 with a suction cup 220 at the proximal end 10 and a lumen 224 through the longitudinal length 50. The lumen opens into a pore 226 within the suction cup at the proximal end 10 and terminates at the opposite distal end 20 in a rod opening 230. One embodiment includes a plug having a nipple 717 that fits into the rod opening. An alternative embodiment, has an adjustment rod 300 with a proximal end that is moveably inserted into the rod opening. The adjustment rod can be moved into and out of the lumen to control the suction force that can be generated under the suction cup. If the rod or nipple is removed from the lumen, the suction cup is inhibited from generating a suction force, which provides an advantageous safety release mechanism 700 to the lens manipulator. Additional embodiments can include an outer cuff 500 that goes around or partially around the over-sleeve to provide controlled friction against the over-sleeve being removed from the adjustment rod. The cuff can also be used as a control mechanism for adjusting the suction force of the suction cup. An alternative embodiment has the proximal end components, including the proximal end of the adjustment rod and over-sleeve angled relative to the ergonomic structures used to hold the lens manipulator. There are also disclosed embodiments of an over-sleeve with a suction cup having a peripheral edge 60 capable of being deflected so that a continuous leading edge 80 can be used to form a vacuum with a contact lens 5. With these embodiments, there can also be a lumen 224 that traverses at least some portion of the stem and opens onto the suction cup as a pore 226. Each of these general components can have one or more sub-components, which will be discussed in detail below.

In FIG. 1 there is shown one embodiment of a lens manipulator and the various general, components thereof. In this embodiment, the over-sleeve 200 has an elongated stem 210 that terminates in a suction cup 220 at the proximal end 10. The suction cup can be formed as part of the stem to form the over-sleeve. Alternatively, the suction cup can be a separate component that is operably attached to the stem to form the over-sleeve. In one embodiment, the suction cup is centered over the proximal end of the stem, such that the apex 222, or the point furthest from the peripheral edge 60 of the suction cup is aligned with the longitude 50, such as shown, for example, in FIG. 2. In alternative embodiments, the suction cup can be off-set, such that the apex is off-center from the longitude. A person with skill in the art will be able to determine an appropriate off-set distance for the apex to facilitate contact with a contact lens.

Figure 2:
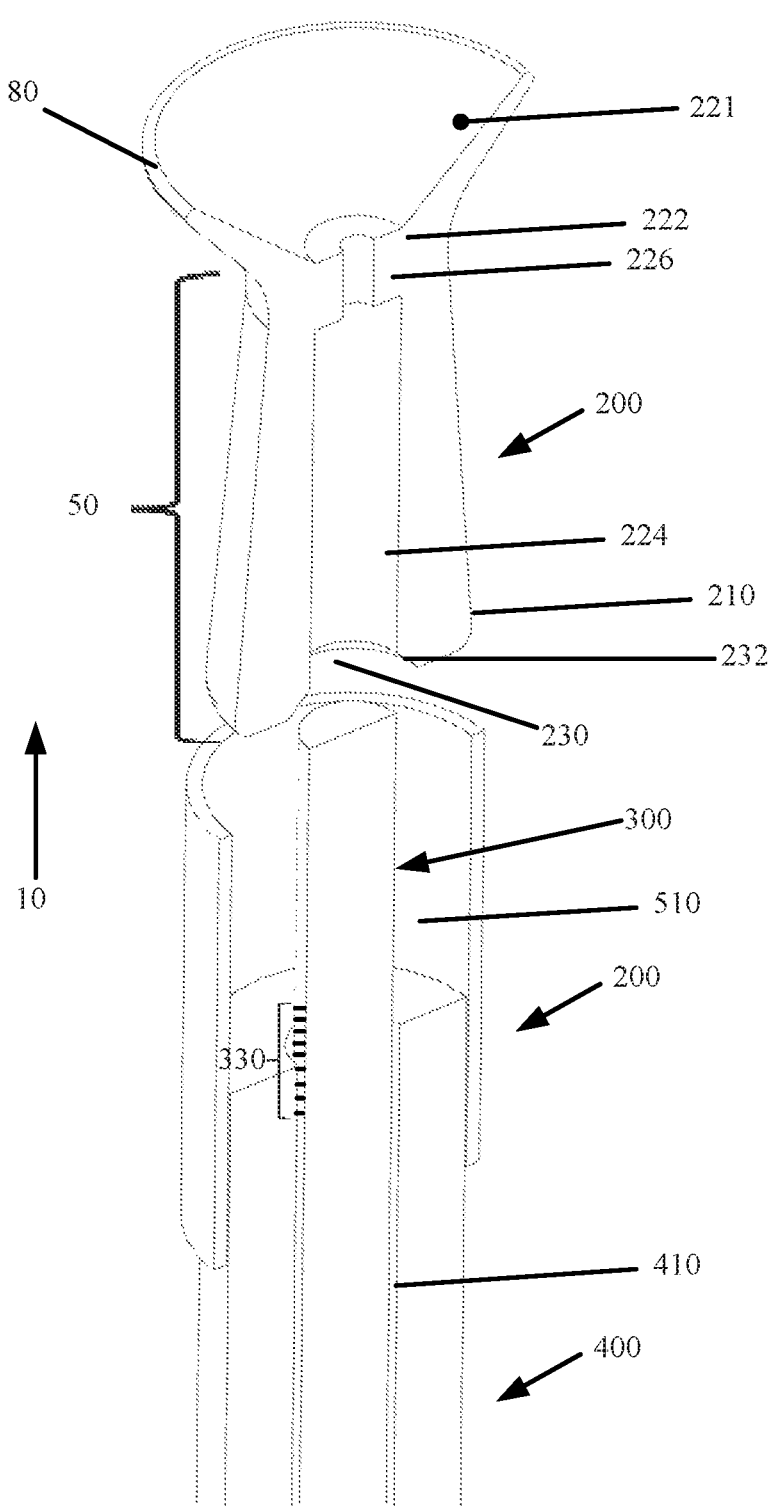
FIG. 2 is an enlarged cut-away view, taken along line 2-2' of the distal end of an embodiment of a lens manipulator, according to the subject invention. In this view, the over-sleeve is shown pulled disengaged from the adjustment rod.
Figures 3A, 3B:
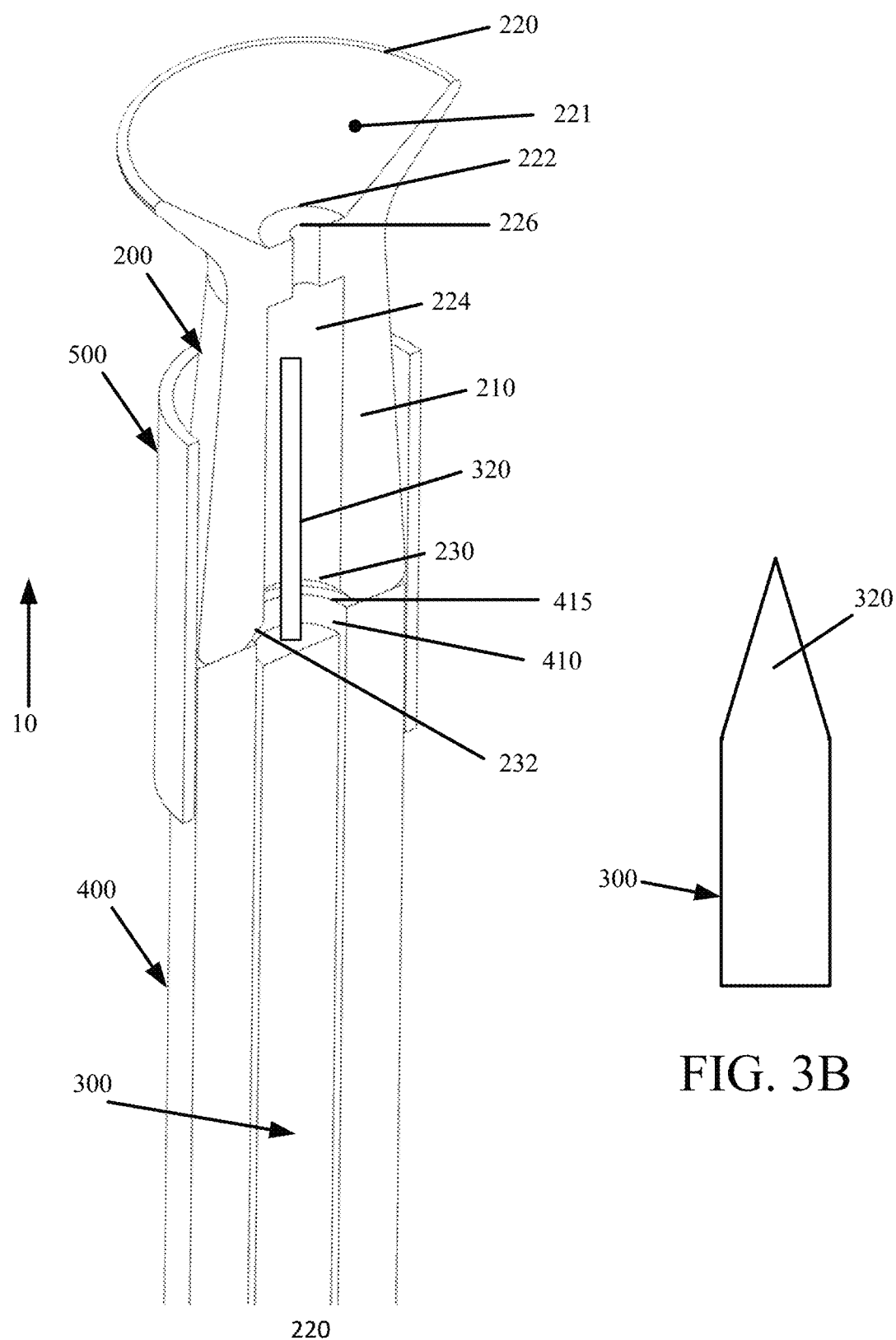
FIG. 3A is an enlarged cut-away view, taken along line 2-2' of the distal end of an embodiment of a lens manipulator, according to the subject invention. In this view, the lens manipulator is shown seated in the friction sleeve and the adjustment rod is removed from the lumen. Also shown is an embodiment of an alignment tip.
FIG. 3B shows an alternative embodiment of an alignment tip on an adjustment rod.

In another embodiment, the stem has a lumen 224 that extends the full longitudinal length 50 of the over-sleeve. In a further embodiment, the proximal end 10, the lumen can terminate within the concavity 221 of the suction cup. In yet a further embodiment, the distal end 20, the lumen can terminate in a rod opening 230 into which the proximal end 10 of the adjustment rod 300 can be inserted. In a further embodiment, the proximal end of the lumen narrows at the pore 226, so that the diameter of the pore is less than the diameter of the lumen. An example of this is shown in FIGS. 2 and 3A.

The suction force generated by a suction cup is caused by the difference in air pressure between the outside and inside of the cup and the surface area of the object covered by the concavity 221 of the suction cup. Changing one or both of these factors can affect the suction force produced by the suction cup. In one embodiment, the lumen 224 can be used to adjust the difference in air pressure between the outside and the inside of the suction cup. By moving the adjustment rod into or out of the lumen, the air pressure that can be generated under the suction cup can be altered, thus adjusting the release force to individual needs and preferences. In one embodiment, the diameter of the lumen is such that the adjustment rod is friction fit in the lumen, but can be slidably adjusted in the lumen to change the total volume of the lumen and the concavity 221 of the suction cup. In a further embodiment, the adjustment rod and the lumen form an airtight seal between them, so that ambient air is inhibited from entering the lumen from the rod opening 230. Moving the rod into and out of the lumen to change the volume between the suction cup and the adjustment rod thereby changes or alters the maximum suction force that can be formed by the suction cup with a contact lens. In one embodiment, the maximum suction force generated by a suction cup for attachment to a contact lens is at least 20 g, 25 g, 30 g, 35 g, 40 g, 45 g, 50 g, 55 g, 60 g, 65 g, 70 g, 75 g, 80 g, 85 g, 90 g, 95 g, 100 g, 105 g, 110 g, 115 g, 120 g, 125 g, 130 g, 135 g, 140 g, 145 g, 150 g, 155 g, 160 g, 165 g, 170 g, 175 g, 180 g, 185 g, 190 g, 195 g, 200 g, or a suction within a range between any two of the listed values. In a specific embodiment, the maximum suction force to be generated between a contact lens surface and a suction cup of the subject invention is approximately 115 grams.

The dimensions of an adjustment rod and lumen can depend upon a variety of factors, including, but not limited to, the type of contact lens it will be used with, the amount of force necessary to secure a contact lens for insertion and removal, the dimensions of the suction cup, and other factors understood by those with skill in the art. In one embodiment, the lumen 224 has a longitudinal length 50 of between approximately 5 mm and approximately 20 mm. In a more specific embodiment, the lumen has a longitudinal length of between approximately 10 mm and approximately 15 mm. In another embodiment, the adjustment rod 300 has a length of between approximately 5 mm and approximately 15 mm. In a more particular embodiment, the adjustment rod has a length of between approximately 8 mm and approximately 13 mm. In a specific embodiment, the adjustment rod has a length of about 10 mm.

Suction cups typically have a continuous, pliant outer or peripheral edge 60 to create a seal against the surface of a contact lens 5, which allows a vacuum to be formed under the suction cup when air is removed or forced out. While this can be advantageous when handling a lens for extraction, it can inhibit use of the suction cup for insertion, because of a slight suction force that can be formed when depositing the lens onto the eye surface. This small suction force can be sufficient to inhibit a successful insertion and release of the contact lens.

Figure 15:
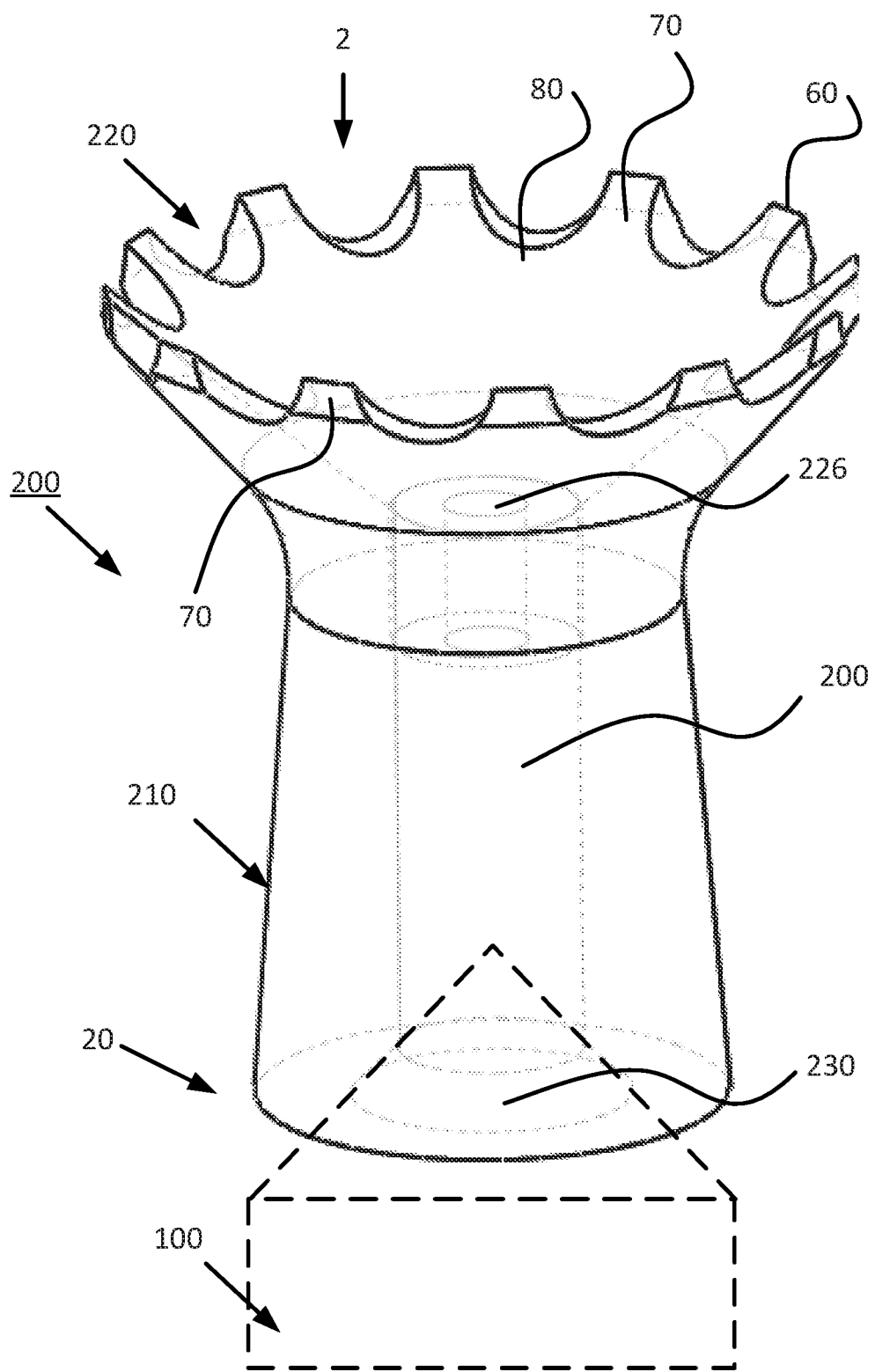
FIG. 15 is an isometric view of an embodiment of a suction cup with an interrupted or discontinuous leading edge, according to embodiments of the subject invention.
Figure 16:
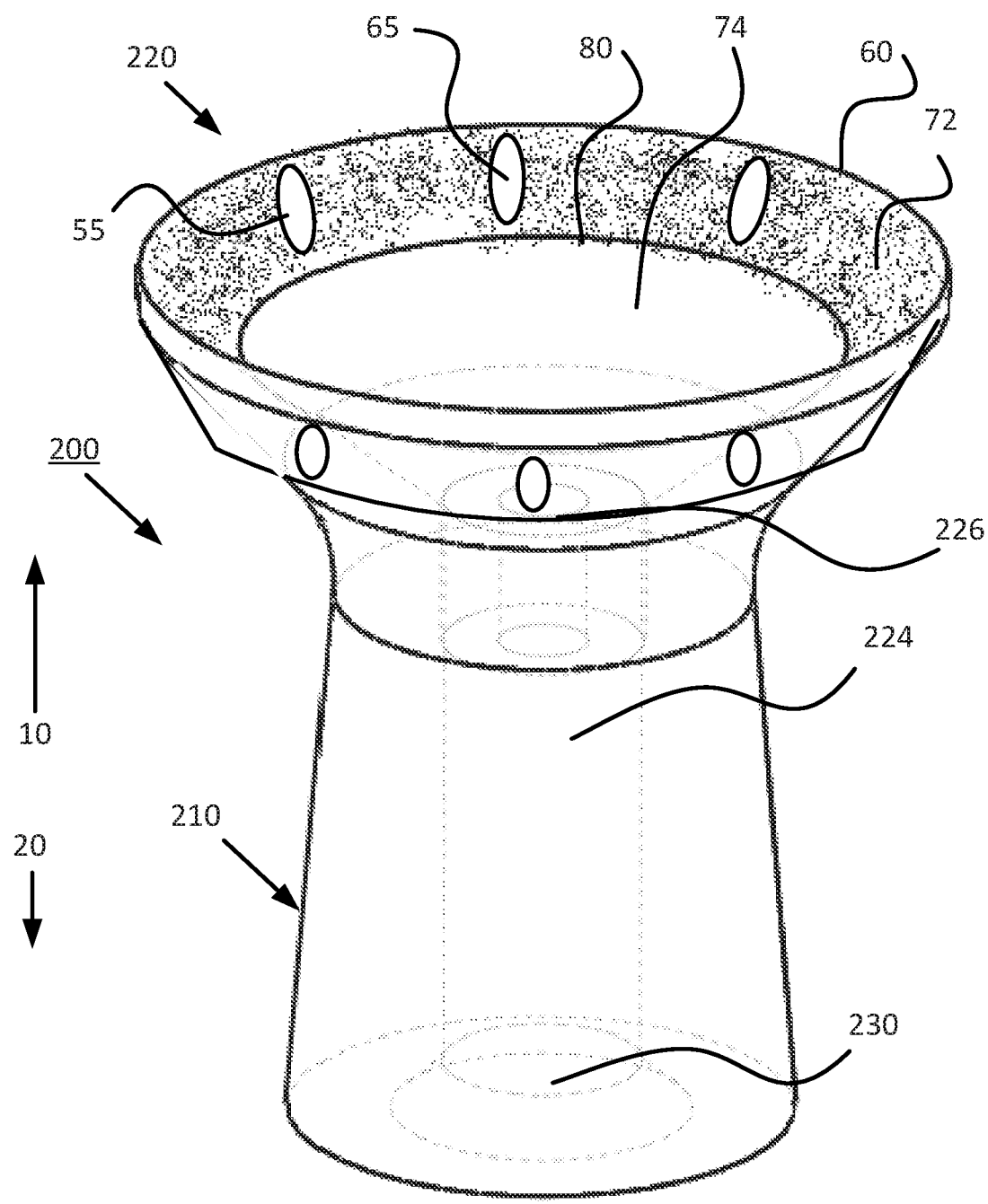
FIG. 16 is an isometric view of an embodiment of a suction cup with a leading edge having a surface texture and holes or vents, according to embodiments of the subject invention.

In an alternative embodiment of the subject invention, a suction cup 220 can have various types of discontinuities 70 around the peripheral edge 60. For example, the peripheral edge can have one or more lobes, petals, fingers, teeth, or be otherwise interrupted, serrated, indented, or have any of a variety of uneven or non-uniform edge, such as shown, for example, in FIGS. 15, 19A, 19B, 20, 21 and 22. In an alternative embodiment, the discontinuities can be holes, fenestrations, openings or other types of vents 65 around the peripheral edge that allow air to circulate into the suction cup when a contact lens is disposed on the discontinuous peripheral edge, thereby inhibiting forming a seal when small forces act on the suction cup and when the peripheral edge is not deflected or deformed. FIG. 16 illustrates a non-limiting example of vents around the peripheral edge of a suction cup 220. The discontinuities 70 in the peripheral edge and/or vents can allow the suction cup to support the weight of a contact lens and materials that may be deposited therein, such as, for example, saline solutions or medicaments, while inhibiting the peripheral edge from forming suction with the contact lens, therefore allowing easier release of the contact lens 5A at the time of deposition on an eye.

Figure 19A:
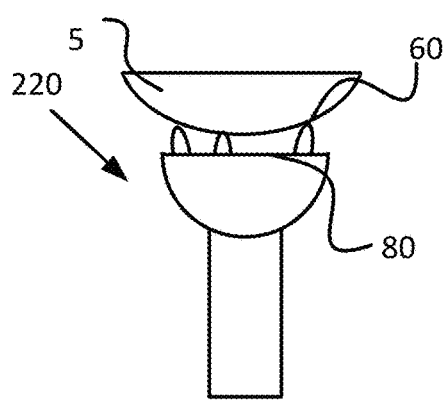
FIGS. 19A and 19B are representative views of a contact lens placed on an embodiment of a suction cup device, according to the subject invention.
Figure 19B:
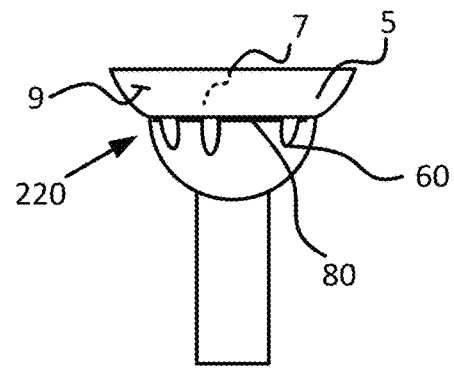

In one embodiment, the convex side of a contact lens can be gently placed on the discontinuities 70 around the peripheral edge 60, as shown, for example, in FIG. 19A, such that the peripheral edge is inhibited from being deformed or altered in shape. Thus, the peripheral edge 60 should have sufficient rigidity to support the weight of a contact lens and any fluids or materials in the concavity 221. The rigidity should allow the contact lens to rest on the peripheral edge of the discontinuities, so that there is minimal contact with the convex surface 9 of the contact lens. FIG. 19A illustrates one example of this arrangement of a contact lens on a plurality of discontinuities around a peripheral edge.

When the contact lens is placed on the cornea of the eye, the peripheral edge can be easily disengaged from the contact lens with minimal or no force. As will be discussed below, the peripheral edge 60, while sufficiently rigid to support a contact lens, can also have a "moment of flexion" or "bending moment" at which the rigidity of a discontinuity 70 is overcome by applied forces and causes the peripheral edge to be deformable or deflectable, such that it can be moved out of the way to expose a continuous edge 80. Such moment of flexion or bending can be an instantaneous or almost instantaneous reaction to applied force. Alternatively, it can be a gradual bending or deformation of the discontinuities in response to applied forces.

Extraction of a contact lens with a suction cup usually necessitates that suction be formed between the outer convex surface 9 of a contact lens 5 and the inner concavity 221 of a suction cup. The methods for forming suction under a suction cup are known in the art. In one embodiment, the discontinuities 70 arise from the continuous edge 80. For example, the discontinuities that form a peripheral edge and continuous edge can be formed from the same material, such that the peripheral edge and continuous edge are integral or continuous with each other, such as shown, for example in FIG. 15. In an alternative embodiment, the discontinuities arise from a different area or position on the suction cup, such as next to or beside the continuous leading edge. For example, the discontinuities can arise from around the outside or convex surface of the suction cup and extend above the continuous leading edge 80, such as shown, for example, in FIG. 16. At the time of extraction, the suction cup 220 can be pressed against the contact lens causing the peripheral edge 60 to be deflected so that a leading edge 80 there below can contact the convex surface 9 of the contact lens. More specifically, at the time of extraction the cup can be pressed against the contact lens such that the discontinuous peripheral edge is deflected or pushed radially outward, away from the concave surface 7 of the contact lens, thereby exposing or otherwise allowing the leading edge 80 to engage the contact lens, so that a seal can be created with the smooth, uninterrupted, continuous leading edge of the suction cup.

The discontinuities 70 of a peripheral edge can be uniformly placed, such that there is an even pattern or distribution of the interrupted peripheral edge 60. FIGS. 15 and 16 illustrate one example of evenly placed discontinuities. In an alternative embodiment, the discontinuities can be unevenly or randomly distributed around the peripheral edge 60 of the suction cup. For example, the discontinuities can be bunched or grouped in certain areas. In another alternative there can be wider gaps or spreading between the discontinuities creating open areas. The arrangement of discontinuities to form a peripheral edge can be determined by a person of skill in the art.

Contact lenses and in particular rigid contact lenses can be more easily extracted when the extraction or pull force is applied eccentrically. A random distribution of discontinuities can assist with extraction or insertion of contact lenses that benefit from eccentric positioning of the suction cup. Eccentric positioning means that the suction cup 220 engages off-center with the convex surface 9 of a contact lens 5. During an eccentric extraction, a more open area of the peripheral edge 60 with fewer, gapped, or no discontinuities can be oriented towards the periphery of the contact lens, so as to minimize contact with the sclera when discontinuities deflect. These same areas can also be beneficial with video-assisted devices such as the CLIARA, disclosed in U.S. Published Application No. 2015/0265467, as the open areas do not interfere with visualization of the contact lens.

Suction cups usually have a smooth surface to ensure an optimal seal is achieved. This smooth surface finish tends to be adherent or "sticky" to the touch, which can be beneficial for contact lens 5 extractions, but can be problematic for contact lens insertion. In one embodiment of the subject invention, a portion of the concave surface 7 of a suction cup can have a non-smooth surface and another portion can have a smooth surface, such that the concave surface has two different surface finishes. With this embodiment, a peripheral band 72, around the proximal end 10 of the concave surface of the suction cup 220, can be stippled, roughened, ridged, or otherwise textured to provide a non-smooth or rough surface to the area of the peripheral band 72, which can form less adhesion to a contact lens convex surface. Further, with this embodiment, there can also be a central region 74, on the concave interior distal 20 to the peripheral band that can stick or adhere to the contact lens surface. The central region can be a smooth surface or can be coated with something that imparts a "sticky" surface to adhere to the contact lens surface. FIG. 16 is an illustration of a suction cup embodiment having a peripheral band 72 and a central region 74. A contact lens positioned against the textured peripheral band 72 of the suction cup can be inhibited from adhering to the textured surface by the inherent surface tension, thereby inhibiting the creation of suction under the suction cup. This can be advantageous when inserting a contact lens as the peripheral edge can release or disengage from the contact lens, therefore allowing a successful insertion.

When extracting a contact lens, the sticky central region 74 can become beneficial. The suction cup can be pushed or pressed onto the contact lens, so as to deflect or push aside the peripheral band 72, allowing the contact lens to make contact with the central portion of the suction cup. The central portion having a smooth edge can form a seal with the convex contact lens surface, therefore forming suction that can also promote successful extraction.

Contact lenses, in particular rigid contact lenses, can be more easily extracted when a force is applied eccentrically. Eccentric extraction force means that the suction cup 220 engages the lens surface at an angle of incidence that is off-center of the contact lens. A contact lens is typically semi-spherical or partially hemispherical in shape. Therefore, an extraction with an off-center angle of incidence means that the suction cup is applied off center of the central axis of the contact lens. The suction cup is applied towards one side of the lens, so that the leading edge can make full contact with the contact lens. In one embodiment, the suction cup attached to a stem and used for manual contact lens extraction has a substantially rigid or non-pliable connection between the suction cup and the stem or handle. When performing an eccentric extraction with manual lens manipulators 100, where the contact lens is conveyed to the eye by hand, the angle of incidence of the cup can be manually adjusted, thereby achieving off-center contact with the contact lens. However, when non-manual, lens manipulators are used, such as the CLIARA device mentioned above, the suction cup used therewith can have a fixed angle of incidence, relative to the eye, and can approach from the front of eye. The angle of incidence is usually centered on the contact lens, or is parallel to the optical axis. Suction cups rigidly attached to a handle or stem can inhibit an eccentric extraction because the suction cup cannot tilt or bend sufficiently to make full contact with the side of the lens.

Figure 17:
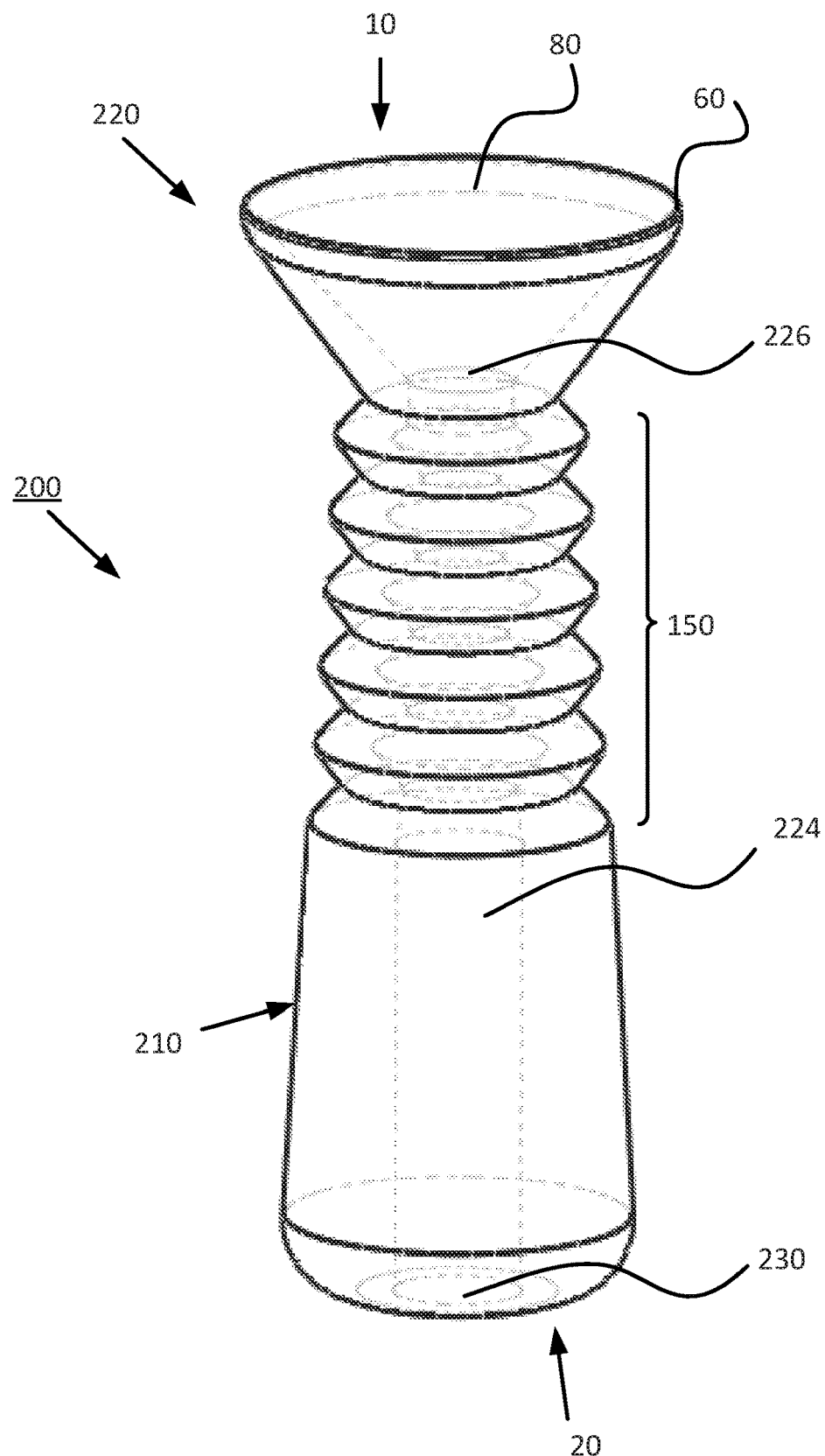
FIG. 17 is an isometric view of an embodiment of a suction cup with flexible neck, according to embodiments of the subject invention.
Figure 18A:
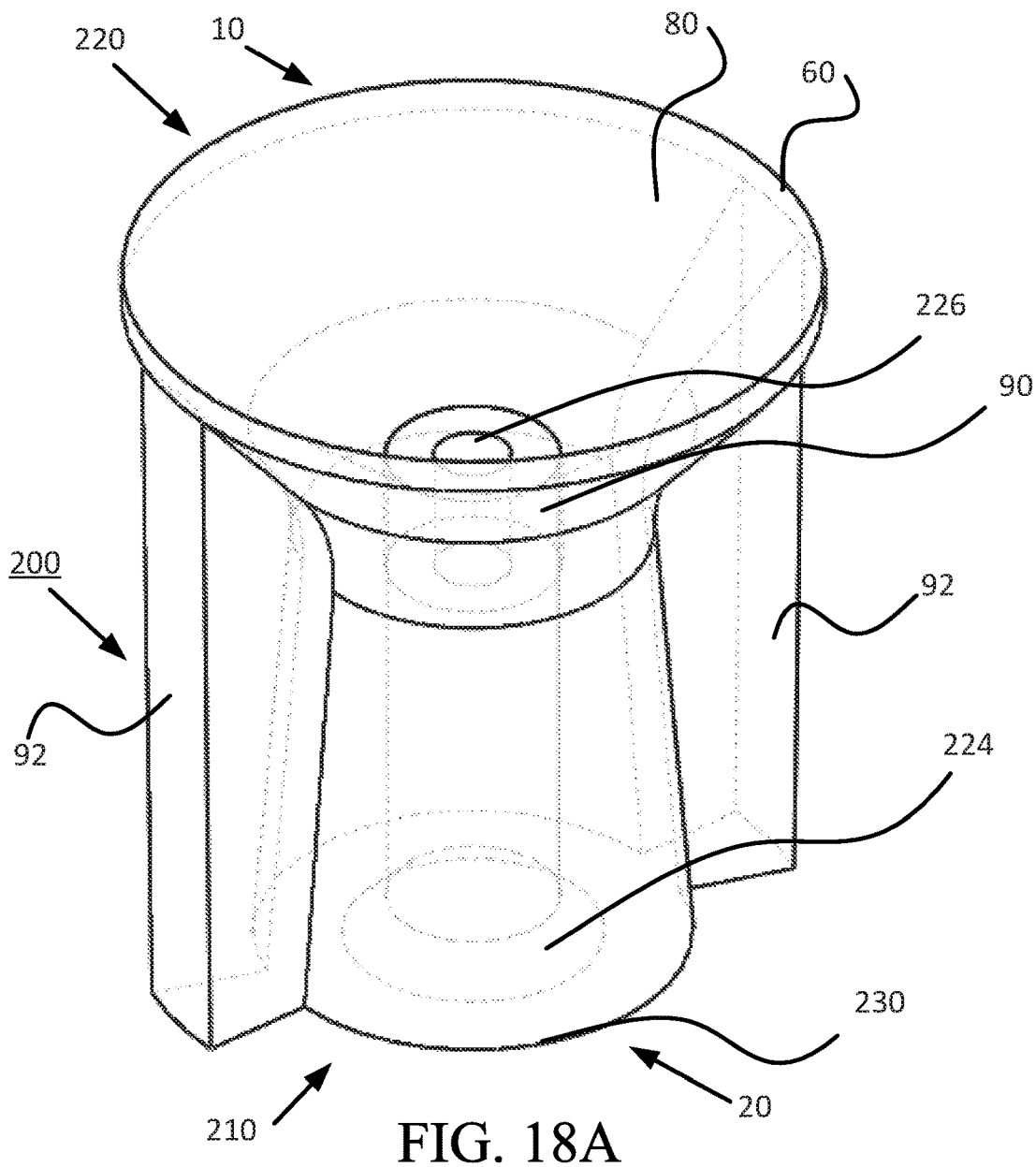
FIGS. 18A and 18B are an isometric view and a side view, respectively, of an embodiment of a suction cup with ribs, according to embodiments of the subject invention.
Figure 18B:
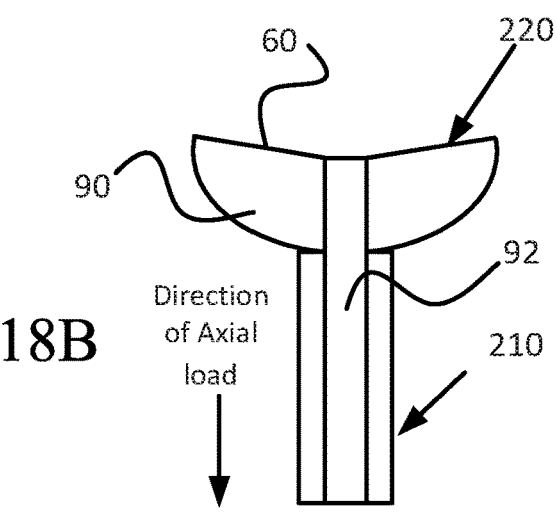

To facilitate bending or tilting of the suction cup 220 relative to the stem 210, there can be a flexible connector 150 between the suction cup 220 and the stem 210. The flexible connector can be sufficiently stiff or rigid to hold the suction cup in position for a linear approach to a contact lens and still be able to flex or bend to facilitate an eccentric connection to the contact lens. In a particular embodiment, the flexible connector has a bendable neck. In a further embodiment, the bendable neck utilizes a bellows-type configuration, such as shown, for example, in FIG. 17. Bellows-type connectors have thinner or narrower areas that provide flexure and thicker or wider areas that inhibit over-flexing and help maintain torsion control. Bellows connectors are known in the art and any of a variety of styles or configurations can be used with the embodiments of the subject invention. As will be discussed below, bellows-type connectors can be advantageous for a stem having a central channel and can inhibit the interior lumen from collapsing under bending loads and/or vacuum pressures.

Another characteristic of suction cups is that they can generate an even or uniform suction around the circumference of the suction cup when attached to a contact lens. This is due to the rotationally symmetric designs, and a theoretical axial pull that deforms the cup uniformly. Thus, deforming the circumference of the suction cup can degenerate the uniformity of the connection and release the vacuum. Likewise, soft contact lenses can be more effectively released from the eye by not only pulling the lens perpendicular to the eye, but also by pinching the lens, so as to deform the shape and allow air to enter the eye-lens interface and break suction force between the eye and lens.

When utilizing a suction cup to remove a contact lens, it can be difficult to engender a pinching or deforming action with the operation of the suction cup. To mimic the pinching effect, the force applied to the peripheral edge 60 of the suction cup by the pull force or axial load can be applied in a non-uniform manner. This can encourage areas of different pliability on the peripheral edge 60 of the suction cup to deform in stages or at different times, as the pull force is applied to the suction cup. More pliable areas of the suction cup can deform, causing them to pull against other less pliable areas, which deforms the peripheral edge and can promote the ingress of air between the eye and contact lens interface.

In one embodiment, the suction cup has one or more areas that are rigid, less pliable, non-flexible, or otherwise inhibit the peripheral edge in those areas from deforming when pull force is applied to the suction cup. When a pull force is applied, usually with the stem 210 attached to the center of the suction cup, the center of the suction cup is pulled away from the contact lens, consequently elongating the suction cup. The non-pliable areas of the suction cup and peripheral edge can be deformed and pulled away from the contact lens first, thereby forming a pucker or fold in the contact lens that allows ingress of air between the eye and contact lens interface.

In a further embodiment, there are one or more rigid sections on the suction cup. The rigid sections can be in the form of radial ribs 92 that extend along the outside surface 90, to create an intentional uneven deformation of the cup upon application of pull force. In one embodiment, there are two radial ribs positioned approximately 180 degrees apart. The areas of the suction cup that are supported by the radial ribs will be inhibited from deforming or will deform less than other areas of the suction cup. Upon application of pull force, the suction cup will try to elongate and the peripheral edge of the suction cup can experience an inward radial force pulling towards the center. The radial rib supported areas will have more resistance to this force compared to the un-supported areas. Therefore the opposing unsupported regions will be drawn inward, generating a biased deformation of the peripheral edge 60, which will help create a pinching, folding, or puckering action. Continued pulling can cause the areas supported by radial ribs to disengage from the surface first, since they can be less prone to deforming and being drawn into the center of the suction cup. When these areas disengage, air can enter under the suction cup and break the suction.

A contact lens can form a strong adherence to the surface of the eye. This can be beneficial when wearing the contact lens. However, when removing the contact lens, such strong adherence can inhibit the removal of the contact lens. Unfortunately, it is not always possible to know in advance if a contact lens has formed a particularly strong adherence to the eye. When the suction cup 220 is placed against the contact lens on an eye, the suction cup can be pushed against the contact lens to form the suction force, by forcing air out of the concavity 221 under the suction cup. Once this suction force is generated, it can be difficult to remove the suction cup from the contact lens without applying a significant, and potentially harmful, amount of pull force against the suction cup which is therefore transmitted to the surface of the eye.

Embodiments of the subject invention can provide an advantageous safety mechanism by which the suction cup can be removed without application of an excessive amount of pull force against the contact lens. In one embodiment, a friction fit between the adjustment rod 300 and the lumen 224 is configured to cause the adjustment rod to be removed from the lumen if a pre-determined amount of pull force is applied to the lens manipulator. When the adjustment rod is pulled from the lumen, the lumen volume fills with ambient air, thereby equilibrating the external pressure and the internal pressure of the suction cup. This eliminates the suction force on the contact lens, so that the now stand-alone over-sleeve can be manually removed or may self-release from the contact lens. In one embodiment, the diameter of the adjustment rod is at least 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, and 3.5 mm, or a diameter that is a range between any two of the listed values.

Once the over-sleeve has been removed, the rod can be reinserted into the rod opening to, again, be used to adjust the volume of the lumen. In one embodiment, the distal end of the rod opening 230 has a bevel or chamfer 232 around it to aid in insertion of the adjustment rod. FIGS. 2 and 3A illustrate an example of a rod opening with a chamfered edge.

Figure 4:
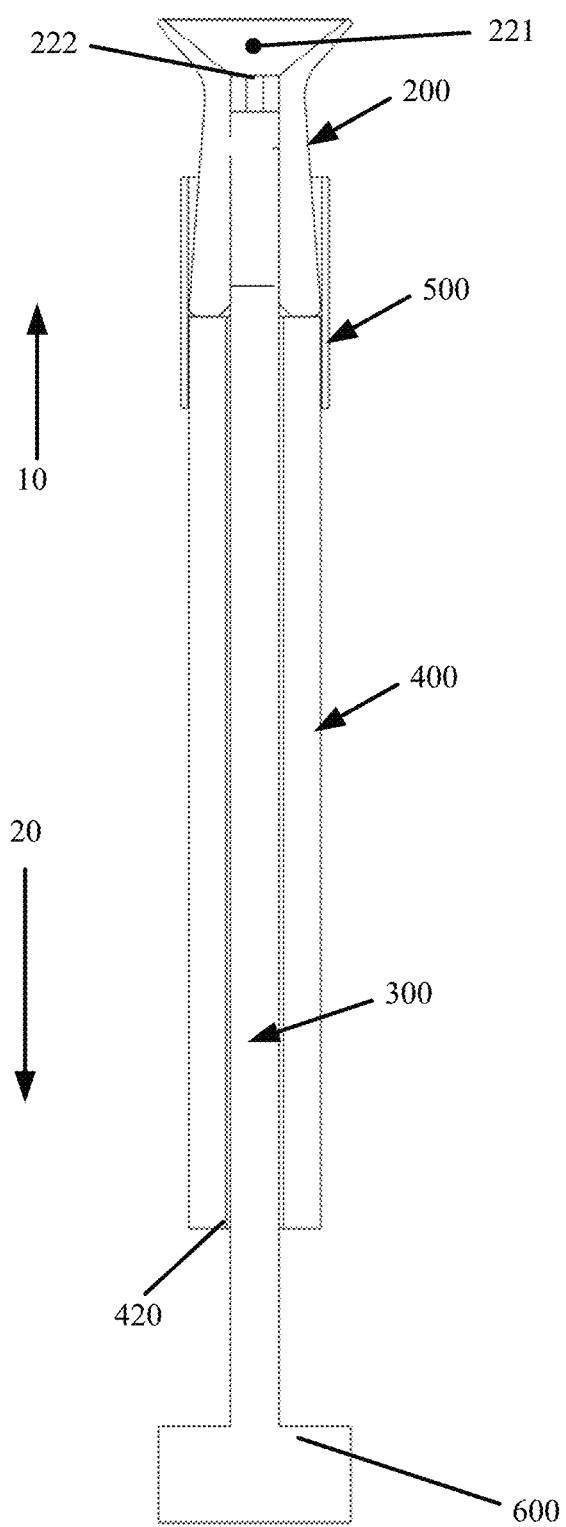
FIG. 4 shows a front elevation view of an embodiment of a lens manipulator.

As mentioned above, the ability to remove the adjustment rod 300 from the lumen 224 can provide an advantageous safety mechanism for releasing the suction force in the suction cup, thereby preventing undesirable or excessive pulling force on the eye and/or contact lens thereon. In order to ensure quick release of the suction force, the adjustment rod can be inserted into the lumen a sufficient distance to block the lumen and allow the suction force to be formed, but not so great a distance that it cannot be quickly removed to release the suction. FIG. 4 illustrates an example of an adjustment rod inserted into the lumen a sufficient distance to allow suction to be formed and still be quickly removed from the lumen.

Depending upon the dimensions and configuration of the over-sleeve, an adjustment rod can fill a small portion, for example, less than 50%, of the volume of the lumen 224. The remaining open space of the lumen can cause more suction force than necessary to be formed under the suction cup. In one embodiment, the proximal end 10 of the adjustment rod can be configured with a spacer 320 to reduce the volume of the lumen, without having to insert the rod further into the lumen. A spacer can be a narrower extension from the proximal end 10 of the adjustment rod. FIG. 3A illustrates one example of a spacer that is narrower than the adjustment rod and juts from the proximal end of the adjustment rod. FIG. 3B illustrates another example of a spacer that is a conical extension at the proximal end of the adjustment rod. Other configurations of spacers are possible and within the scope of this invention. The use of a spacer on an adjustment rod allows the adjustment rod to be inserted as far as necessary to block air flow, be quickly removed, while the remaining volume is reduced to control the maximum suction force that can be formed under the suction cup.

A further advantage of a spacer is that it permits a user to pull the adjustment rod out of the lumen just far enough to allow the ingress of ambient air into the lumen, leaving the spacer in the lumen. This allows the user to replace the adjustment rod in the lumen more easily and, if necessary, without seeing the rod opening, since the spacer can maintain alignment of the adjustment rod and lumen.

The dimensions of a spacer can vary, depending upon the longitudinal length of the lumen 224, the length of the adjustment rod, and how much of the adjustment rod is inserted into the lumen. In one embodiment, the dimensions of a spacer are such that, when the adjustment rod is positioned within the lumen, the spacer reduces the remaining volume in the lumen by between approximately 25% and approximately 85%. In a further embodiment, the dimensions of a spacer are such that, when the adjustment rod is positioned within the lumen, the spacer reduces the remaining volume in the lumen by between approximately 35% and approximately 75%. In a more specific embodiment, the dimensions of a spacer are such that, when the adjustment rod is positioned within the lumen, the spacer reduces the remaining volume in the lumen by between approximately 45% and approximately 65%. In a specific embodiment, when the adjustment rod is positioned within the lumen, the spacer reduces the remaining volume in the lumen by approximately 50%.

The overall length of an over-sleeve can depend upon the required length of the lumen, the dimensions of the suction cup, the length of the stem, and other factors known to those having skill in the art. In one embodiment, the overall length of an over-sleeve is between approximately 20 mm and approximately 60 mm. In a specific embodiment, the overall length of an over-sleeve is approximately 25 mm.

Once it has been determined how much of the length of the adjustment rod 300 should extend into the lumen, to provide the desired maximum suction force, it can be beneficial for that specific length to be set or fixed for the lens manipulator during use. In one embodiment, there can be visual indicators 330 on the rod that can be used to determine how much of the adjustment rod extends into the lumen. For example, graduated marks on the adjustment rod can be used to check the amount of adjustment rod in the lumen. FIG. 2 illustrates a non-limiting example of visual indicators. A friction fit between the adjustment rod and lumen can aid in maintaining the length where indicated.

FIGS. 2 and 4 illustrate embodiments where the adjustment rod and over-sleeve are collinear with the longitudinal length 50 of a lens manipulator 100. These embodiments allow the lens manipulator to be held substantially vertical or perpendicular to the ground, with the suction cup of the over-sleeve directed upwards for use. In use, the lens manipulator can be held in one hand in front of the body. By bending forward, towards the hand holding the lens manipulator, the eye can be brought into proximity with the suction cup to install or remove a contact lens on the eye.

FIGS. 8-14 illustrate an alternative embodiment where a portion 310 of the proximal end 10 of the adjustment rod 300 is bent, turned, or otherwise angled away, relative to the distal end 20 of the adjustment rod. Thus, an over-sleeve 200, when positioned over the adjustment rod 300 can be non-collinear with the longitude 50 of the lens manipulator. With this embodiment, the distal end 20 of the lens manipulator can be held so that the hand holding the lens manipulator is at least partially out of the line of sight when the suction cup is directed upwards for use. This arrangement is ergonomically advantageous and inhibits the hand from interfering with viewing the suction cup as the eye approaches. It also allows one or more fingers on the same hand that holds the lens manipulator to be used for pulling an eyelid away from the eye while simultaneously advancing the contact lens towards the eye. Thus, both hands are not required to be used for moving the eyelid and holding the lens manipulator.

Figure 8:
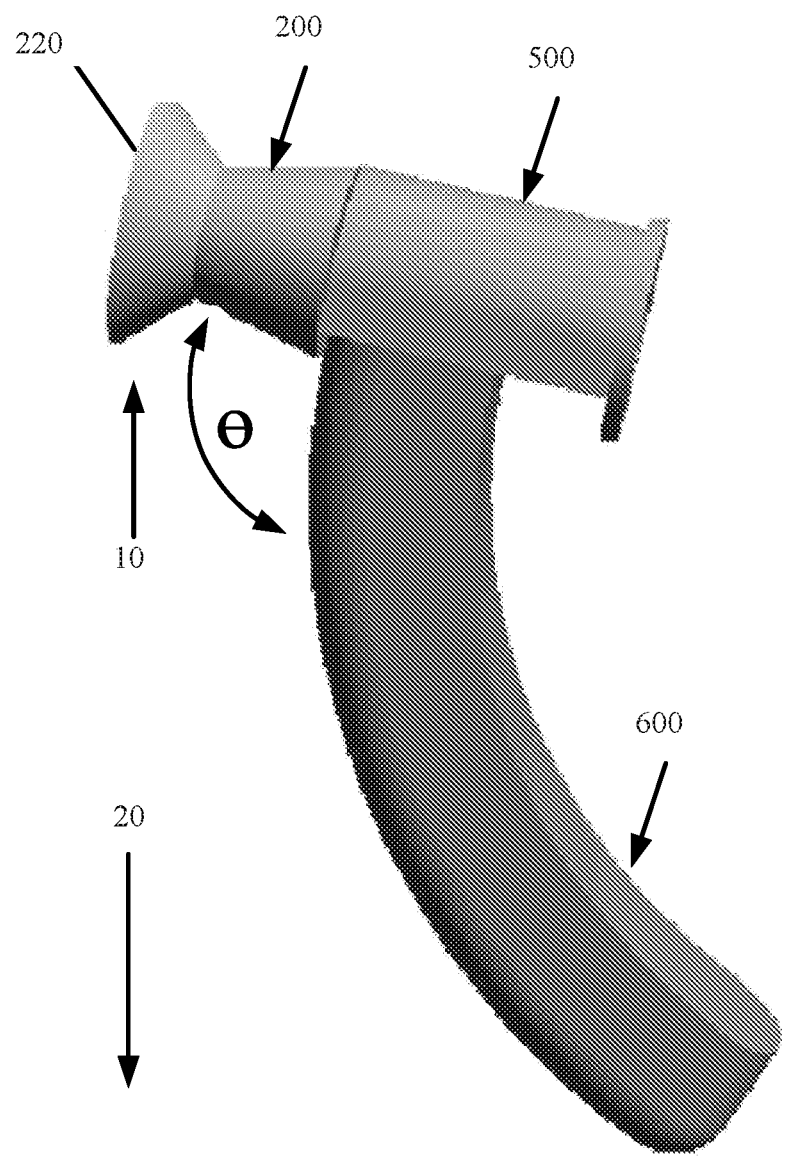
FIGS. 8, 9, and 10 are images of another alternative embodiment of a lens manipulator, wherein the proximal end of the adjustment rod, the over-sleeve, and the cuff are turned approximately 90° relative to a handle portion.
Figure 11:
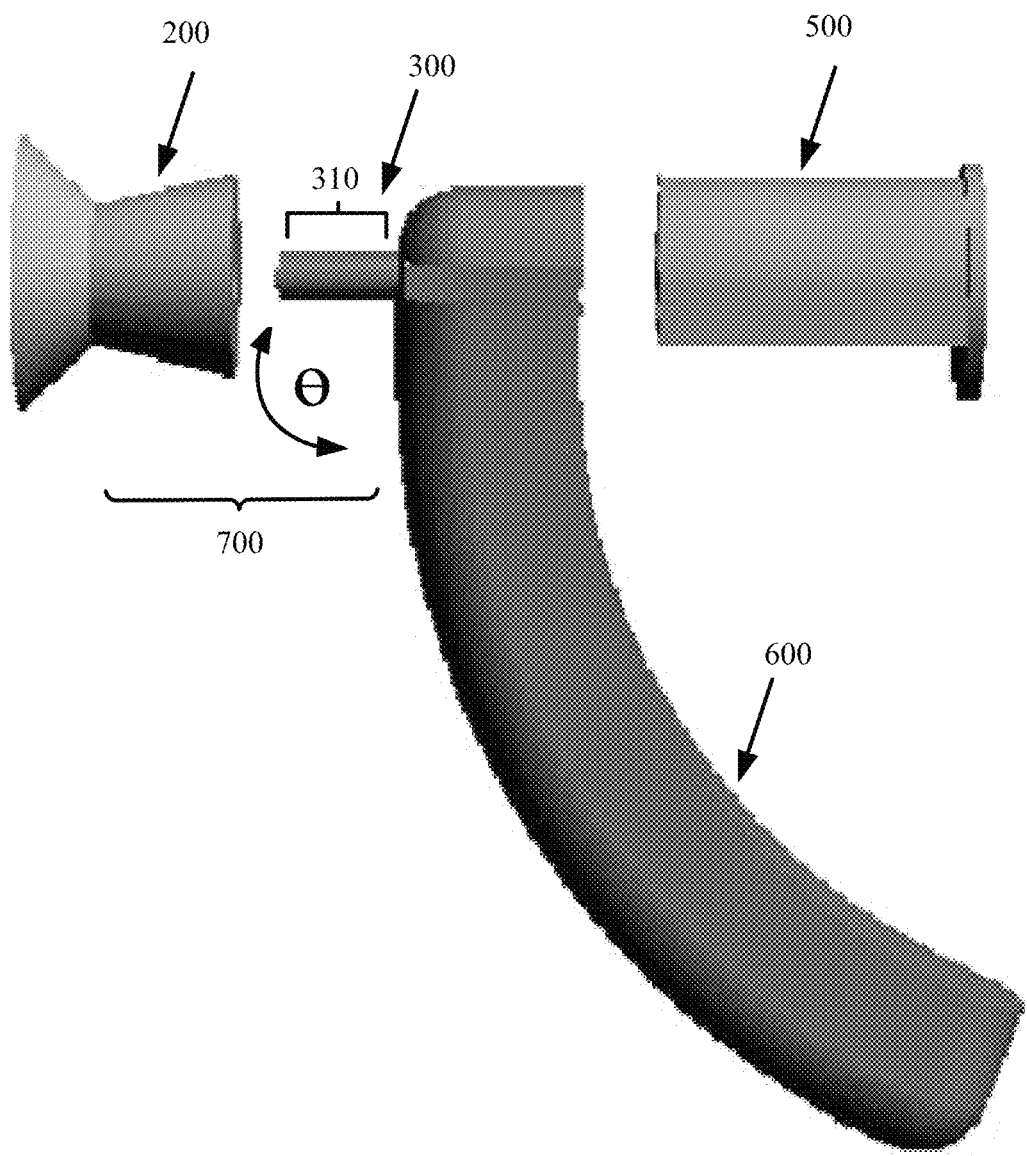
FIGS. 11, 12, 13, and 14 are exploded views of the alternative embodiment in FIGS. 8, 9, and 10.
Figure 12:
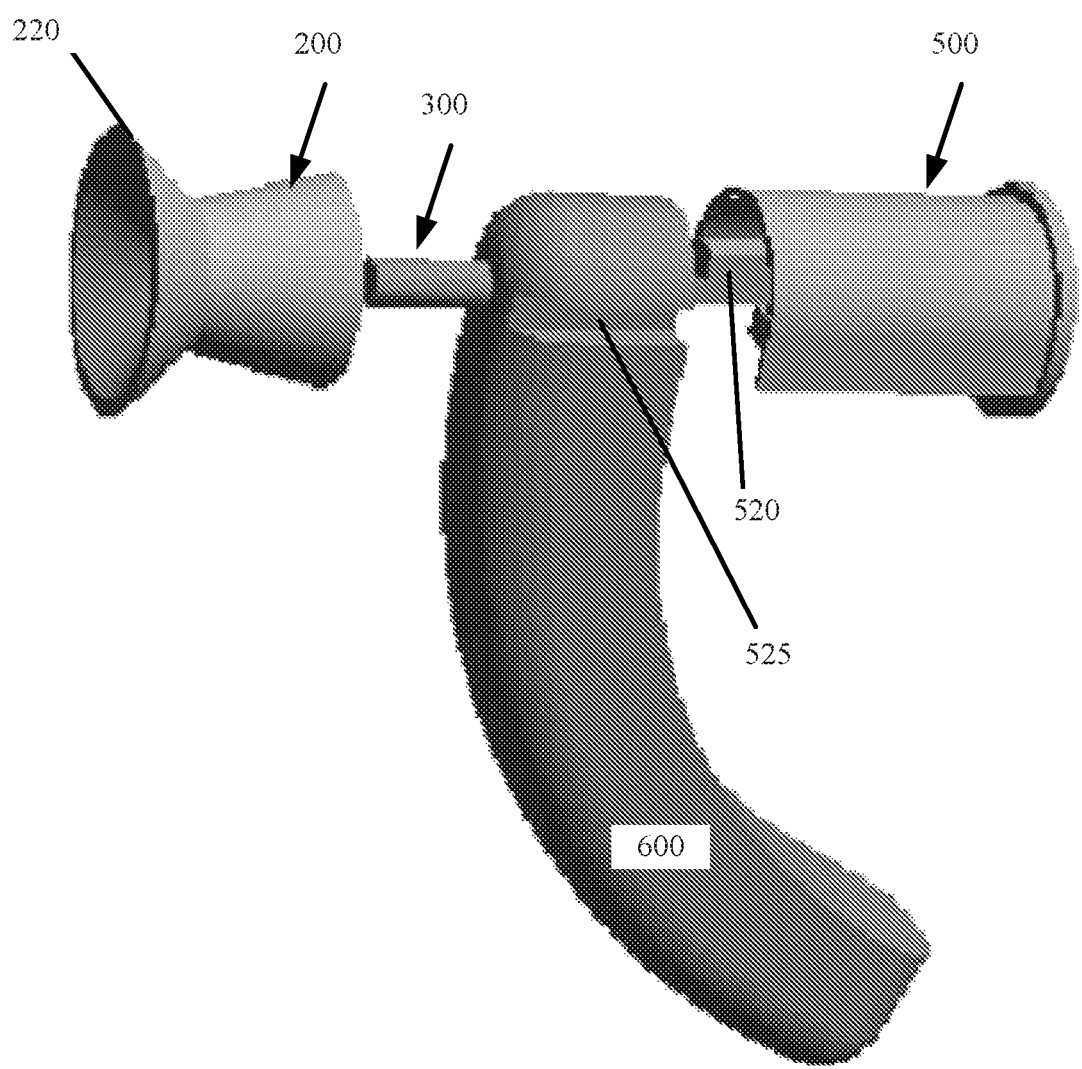

In one embodiment, the bent portion 310 at the proximal end of the adjustment rod has an angle ($\theta$) of between approximately 10° and approximately 120° relative to the longitudinal length or the distal end of the adjustment rod as demonstrated in FIGS. 8 and 11. In a more particular embodiment, the bent portion at the proximal end of the adjustment rod has an angle of between approximately 30° and approximately 110° relative to the longitudinal length or the distal end of the adjustment rod. In specific embodiment, the bent portion at the proximal end of the adjustment rod has an angle of between approximately 80° and approximately 100° relative to the longitudinal length or the distal end of the adjustment rod. In a specific embodiment, the bent portion at the proximal end of the adjustment rod has an angle of approximately 90° relative to the longitudinal length or the distal end of the adjustment rod. One non-limiting example of this specific embodiment is shown in FIG. 12.

In an alternative embodiment, a tensioning sleeve 400 can be used on the adjustment rod 300. In one embodiment, the tensioning sleeve is a generally elongate structure that has a bore 410. In one embodiment, the bore opens onto and forms an aperture 415 at the proximal end 10. There can also be an exit 420 on the distal end 20. The adjustment rod can be frictionally fit into the tensioning sleeve. By moving the adjustment rod into and out of the aperture, the length of the adjustment rod that extends into the lumen can be adjusted. When the over-sleeve is positioned on the proximal end of the adjustment rod, the distal end of the over-sleeve can abut against the proximal end of the tensioning sleeve. Thus, only the length of adjustment rod that extends from the aperture will extend into the lumen of the over-sleeve. FIG. 2 illustrates a non-limiting example of a tensioning sleeve with an adjustment rod extending from the aperture. FIGS. 3A and 4 illustrate non-limiting examples of the over-sleeve sitting on an adjustment rod and abutting the proximal end of the tensioning sleeve.

The frictional fit of the over-sleeve 200 on the adjustment rod 300 can determine the maximum amount of force necessary to pull the rod from the lumen 224. The ability to remove the adjustment rod from the lumen provides an advantageous safety mechanism 700 to prevent excessive and undesirable pulling force being applied to the eye. As discussed above, in one embodiment the rod and the lumen form a friction fit that releases upon application of a predetermined amount of pull force.

Figure 5:
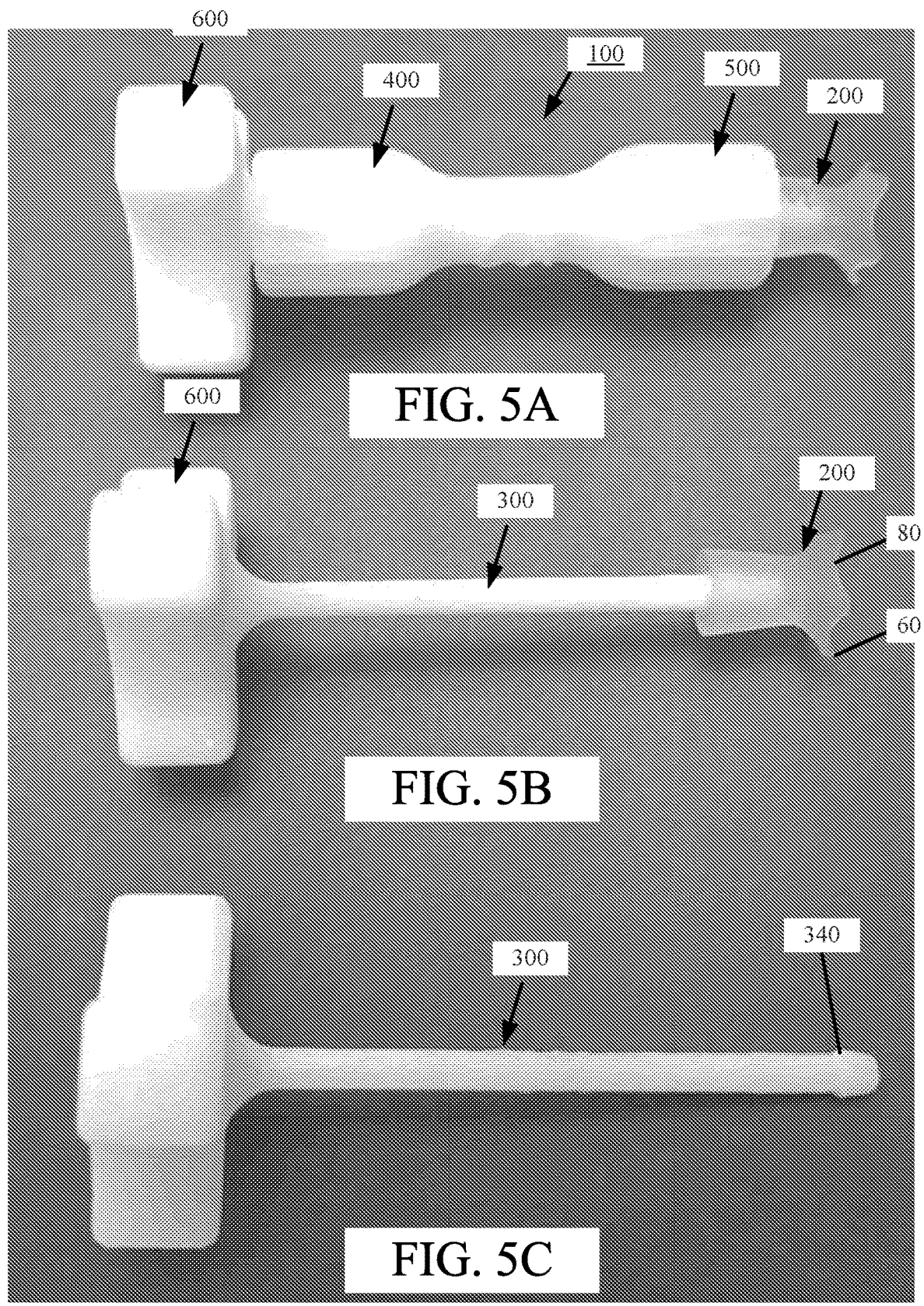
FIGS. 5A, 5B, and 5C show, in a photograph, embodiments of a lens manipulator in different stages of assembly.
Figure 6:
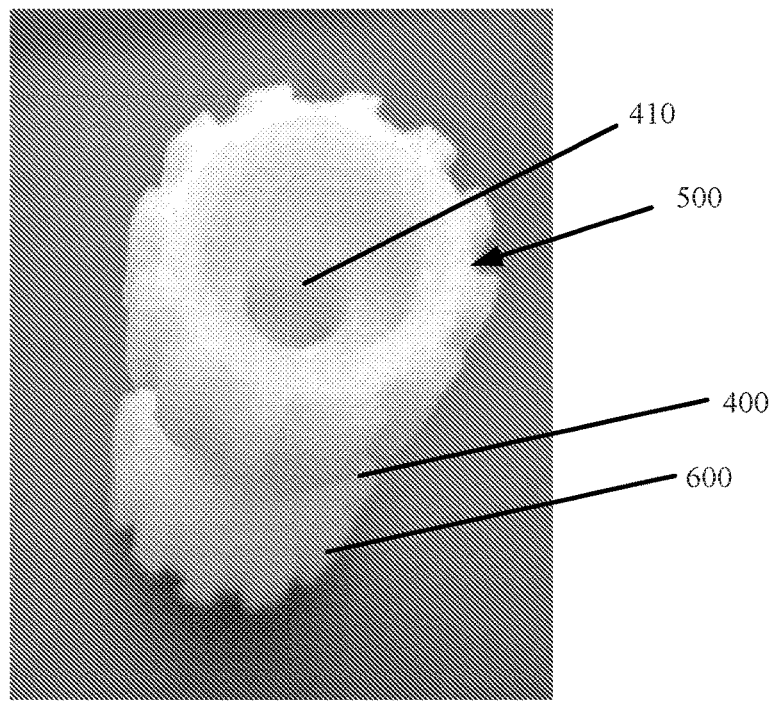
FIG. 6 is a photograph of an embodiment of an over-sleeve.

In another embodiment, a cuff 500 can be used to provide a frictional fit with the over-sleeve. A cuff can be a tubular shape, as shown, for example, in FIGS. 1 and 2, that surrounds a proximal portion of the tensioning sleeve 400 to form a seat 510 around the over-sleeve. In one embodiment, the cuff makes at least partial contact with the over-sleeve positioned in the seat, such as shown, for example, in FIGS. 3A and 4. The cuff can provide resistance to the over-sleeve being lifted off of the adjustment rod. The seat formed by the cuff can also act as a guide for reattaching or reseating the over-sleeve on the adjustment rod. FIGS. 5A and 6 illustrate an alternative embodiment of a cuff that is integral with or formed as part of the tensioning sleeve.

Figures 23A, 23B:
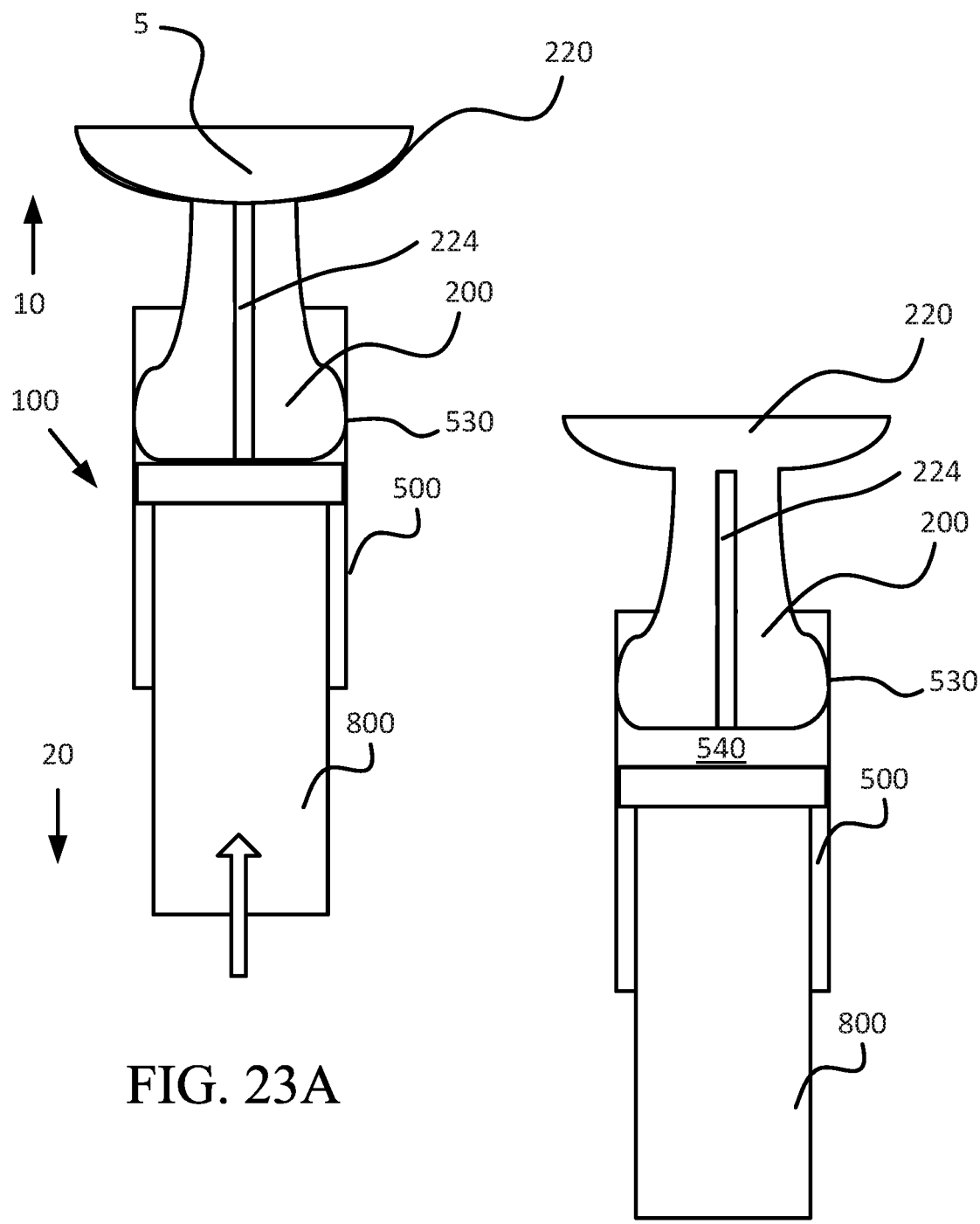
FIGS. 23A and 23B show an alternative embodiment of a lens manipulator that incorporates a plunger with the cuff.

The cuff 500 and the over-sleeve 200 can also be configured to control the amount of suction force formable under the suction cup and also act as a safety mechanism 700. In one embodiment, the stem 210, or at least a portion thereof, when positioned in the proximal end 10 of the bore 510 forms an air tight seal 530 with the cuff. As described above, the suction cup 220 of the over-sleeve 200 can be pushed against a contact lens 5. The air-tight seal permits suction to be created between the two. In a further embodiment, a plunger 800 is disposed at the distal end 20 of the cuff. FIG. 23A illustrates a non-limiting example of this embodiment. The suction that can be formed can be adjusted by how far into the bore 510 of the cuff 500 the over-sleeve 200 is pushed. In FIG. 23A, the over-sleeve is shown positioned against the proximal end 10 of the plunger 800, which can provide the strongest suction force. FIG. 23B shows the over-sleeve distanced from the proximal end of the plunger, which leaves an air-filled void 540 between the plunger and the over-sleeve. This air-filled void can reduce the amount of suction force formable between the suction cup and a contact lens. Changing the volume of the void can change the amount of formable suction.

In the event that the contact lens and the suction cup form too strong a suction, as discussed above, the plunger can be used as a safety mechanism 700 to push the over-sleeve out of the proximal end 10 of the bore 510. When the suction cup exits the bore, the air-tight seal 530 breaks, thereby allowing air into the lumen and eliminating the suction force between the contact lens and the suction cup.

Figure 9:
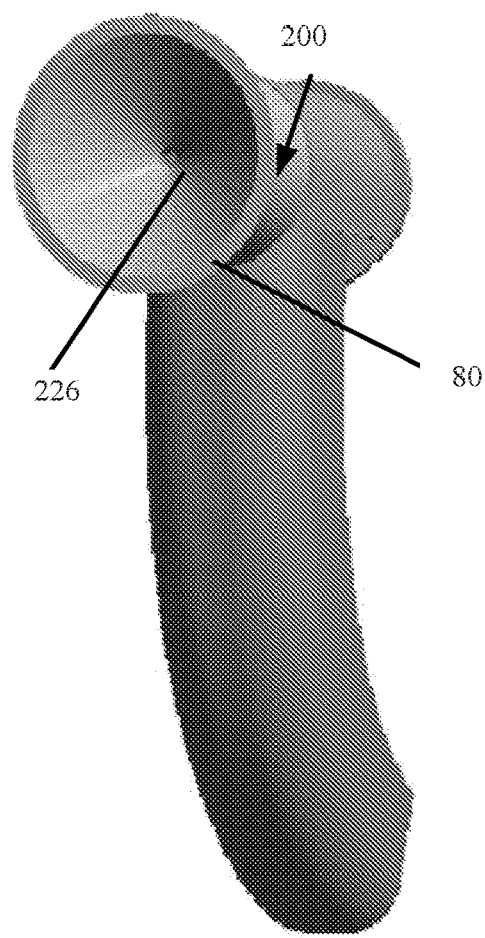
Figure 10:
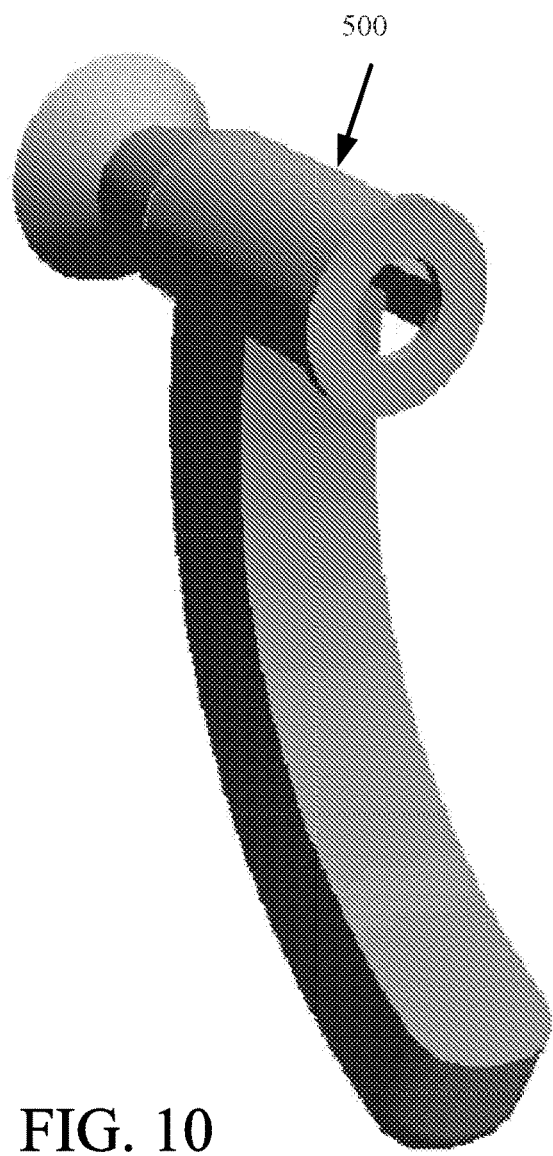

Embodiments having an over-sleeve and adjustment rod that are collinear with the longitude of the lens manipulator, such as shown, for example in FIGS. 1, 3A, 4, 5A, and 6, can also have a cuff that is collinear with the longitude, as shown in FIGS. 2 and 4. Where the adjustment rod has a bent portion 310, the cuff 500 can be rotated relative to the longitude 50, so as to engage with the over-sleeve positioned over the bent portion. FIGS. 9, 10, and 11 illustrate an example of an embodiment with the rotated cuff rotated. With this embodiment, the cuff can be positioned at the same angle as the bent portion 310 and the over-sleeve, so as to be collinear with these components.

Figure 13:
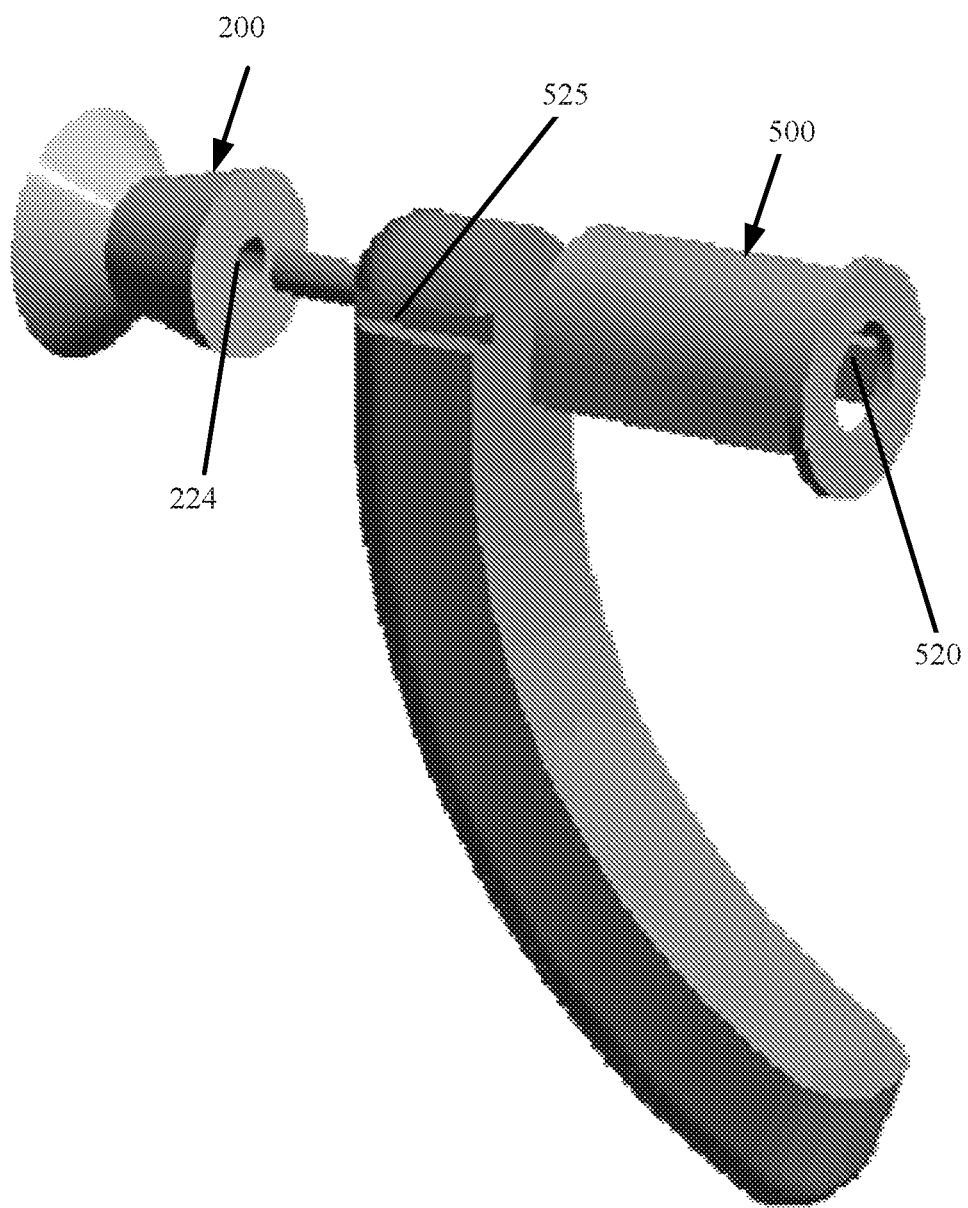
Figure 14:
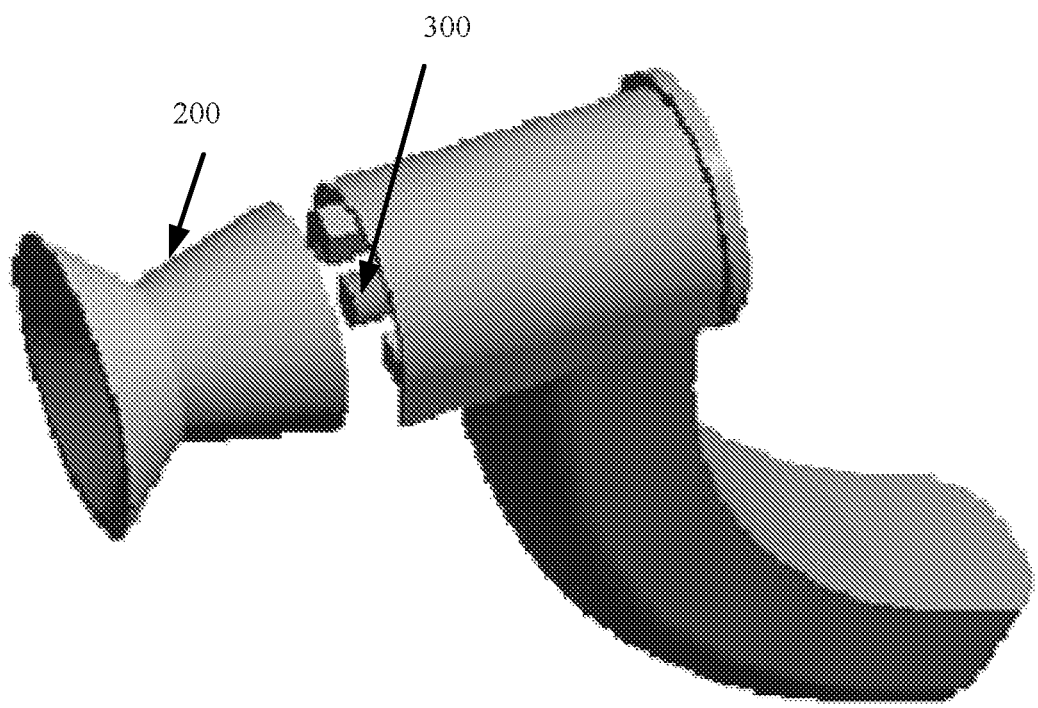

In one embodiment, the cuff is slidably engaged with one or more components of the lens manipulator. For example, the cuff 500 can have a C-shaped circumference, as shown in FIGS. 13 and 15, which allows the cuff to slide over the non-bent portion of the adjustment rod or a tensioning sleeve. In the example shown in FIGS. 13 and 15, the cuff is slidably engaged with an ergonomic feature 600, here shown as a handle. Any of a variety of techniques and devices can be used to slidably engage the cuff with the lens manipulator components. FIGS. 13 and 14 illustrate an embodiment that uses a tongue 520 and groove 525 arrangement. Alternatively, the rotated cuff can be formed or integrated with the lens manipulator and fixed in place.

In yet another embodiment, the adjustment rod 300 can have a detent 340 or enlarged or flared portion at or at about the proximal end 10. The detent can engage with the lumen in the over-sleeve 200. A detent can provide a frictional fit or resistance that inhibits the over-sleeve from being removed from the adjustable rod until or unless a predetermined amount of pull force is applied to the over-sleeve. In a further embodiment, the lumen can be configured with a length that provides the necessary resistance under normal use and allows the over-sleeve to come off the adjustment rod if an excessive pull force is applied to the suction cup. A detent can be any of a variety of surface features or apparatuses that push against or otherwise engage with the wall of the lumen. For example, a flare or detent can be a barb that protrudes outward from the side of the adjustment rod, such as shown in FIG. 5C. By way of another example, a detent can be a spring-loaded ball that retracts into the adjustment rod. Spring-loaded balls used for engaging two objects are well-known in the art and, thus, have not been shown.

Specific frictional forces and/or resistance forces are necessary to maintain the over-sleeve on the adjustment rod during normal use and provide a safety release that allows the over-sleeve to be disengaged from the adjustment rod under certain conditions. The embodiments disclosed herein provide several devices and techniques for configuring and adjusting one or more of these forces. These techniques and devices can be used singularly or in combination.

FIGS. 5A, 5B and 5C illustrate an embodiment that utilizes all of the devices and techniques described herein. FIG. 5A shows an embodiment of a fully assembled lens manipulator that has a tensioning sleeve 400 with a cuff 500 formed at the end of the tensioning sleeve in which an over-sleeve is disposed. FIG. 5B is a partially disassembled view that shows the adjustment rod 300 with the over-sleeve on the proximal end 10. FIG. 5C shows the adjustment rod with the detent at the proximal end that can be used to provide resistance to hold the over-sleeve on the proximal end. With this embodiment, the lumen of the over-sleeve can be configured with a length and diameter that provide sufficient resistance during normal use, but provide a safety release that operates when excessive pull force is applied to the suction cup. Other embodiments can use various combinations of a cuff, adjustment rod, lumen in the over-sleeve, and a detent to achieve the desired frictional and resistance forces.

Figure 7:
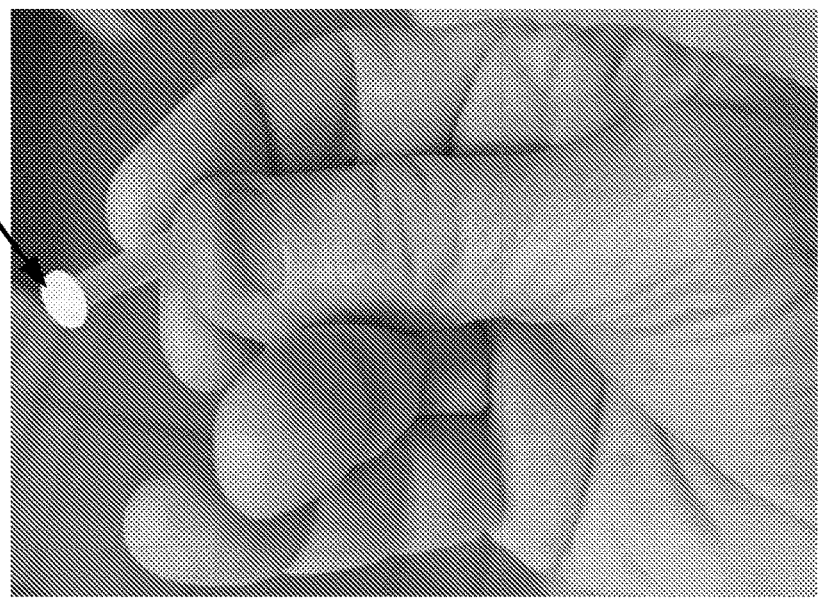
FIG. 7 is a photograph of a lens manipulator held in a hand to show how it can be manipulated.

The embodiments of the subject invention can be used manually. FIG. 7 illustrates how the fingers and palm can be used to hold and control the lens manipulator. In one embodiment, the fingers on one hand can be used to remove the over-sleeve from the adjustment rod, should the safety release not be sufficient. There can be various ergonomic structures 600 on the lens manipulator to assist with holding and manipulating the over-sleeve. FIGS. 5A, 5B, and 5C illustrate an enlarged handle at the distal end 20 of an adjustment rod that can be held in the palm. FIG. 6 illustrates ribbing on the external surface of the cuff and the tensioning sleeve that can assist with holding the lens manipulator. FIG. 7 illustrates a lens manipulator made of a material that forms stiction with fingers. FIGS. 8, 9, and 10 illustrate examples of a handle having an ergonomic curvature that aids in holding and manipulating the position of the over-sleeve and suction cup. It can be advantageous if the ergonomic features 600 allow the lens manipulator to be held in one hand. It can be further advantageous if the ergonomic features allow the lens manipulator to be held such that at least one, preferably two, fingers of the holding hand are free to move the eyelid(s) away from the eye during use of the lens manipulator. For example, ergonomic structures or design can allow the lens manipulator to be held with the thumb and forefinger, thus leaving at least the second and third fingers free to extend forward and move the lower eyelid downward, while the suction cup simultaneously advances towards the eye. Other ergonomic structures that provide the same or similar benefits are within the scope of the subject invention.

The over-sleeves of the subject invention can be stand-alone elements where a passive vacuum is created and maintained by displacement of air under the suction cup, such as, for example, by the deformation of the suction cup. An over-sleeve 200 of the subject invention can be adapted for use with a lens manipulator that utilizes an active vacuum, where vacuum is generated and maintained by active displacement of air under the suction cup with another device, such as a pump or other active suction component. Generation of an active vacuum under the suction cup can necessitate a communication between an active suction component 25, such as, for example, a pump or negative pressure-forming pliable bulb, and the suction cup.

In one embodiment, an over-sleeve 200 of the subject invention has a lumen 224 that extends through the stem 210 and onto the concave surface 7 of the suction cup to form a pore 226 on the concave surface. Thus, the lumen communicates a rod opening 230 at the distal end 20 of the stem 210 with the pore 226 on the concave surface of the suction cup 220. FIGS. 15-18B and 20 illustrate non-limiting examples of over-sleeves 200 adapted with lumens 200. The lumen can be used to cooperatively engage with a suction component 25 of a lens manipulator, as shown, by way of example, in FIG. 20. In one embodiment, the pump or other active vacuum component 25 cooperatively engages with the rod opening 230 of the over-sleeve 200, which communicates with the pore 226 of the suction cup, located at the suction cup concave surface, which comes in contact with the contact lens. This lumen allows an over-sleeve to be used with active vacuum components, such as peristaltic pumps either with negative or positive pressure.

As mentioned above, during extraction of a contact lens, the contact lens can be inhibited from being removed from the eye. This can be caused by a variety of reasons, such as, for example, formation of too strong a suction, insufficient fluid between the contact lens and of the eye, or other phenomenon. Usually, the inability to remove the contact lens is not determined until after a vacuum seal has been formed between the contact lens and the suction cup of an over-sleeve. The lumen can be used as a safety mechanism 700 by which the vacuum formed between the contact lens and suction cup can be released or "broken."

In one embodiment, a safety mechanism 700 can include plug 715 that can be used to block the distal end opening 210 of a lumen 224. The plug can be disposed at the distal end of the stem with a friction fit. The force of the friction fit can be specifically configured to inhibit air from moving through the lumen, but allow the over-sleeve to be or removed from the plug by the force of trying to remove the suction cup and a resistant contact lens.

Figure 20:
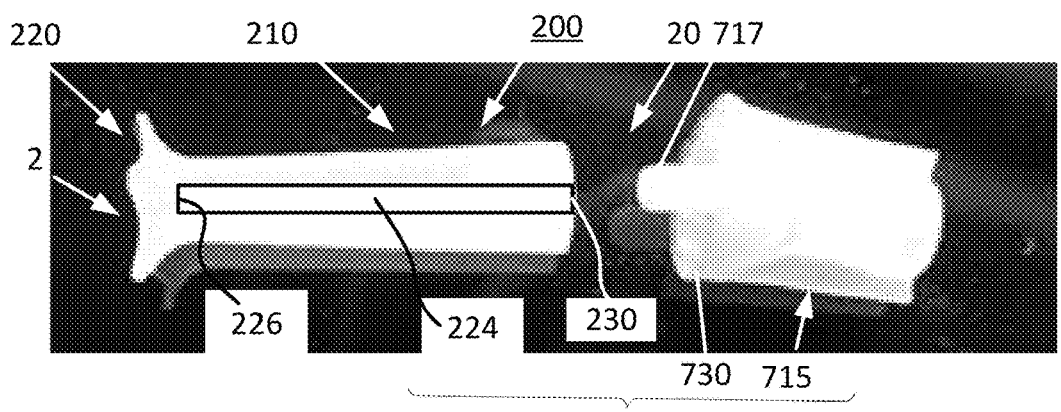
FIG. 20 is a photograph of an embodiment of a suction cup having a safety mechanism, according to the subject invention.
Figure 21:
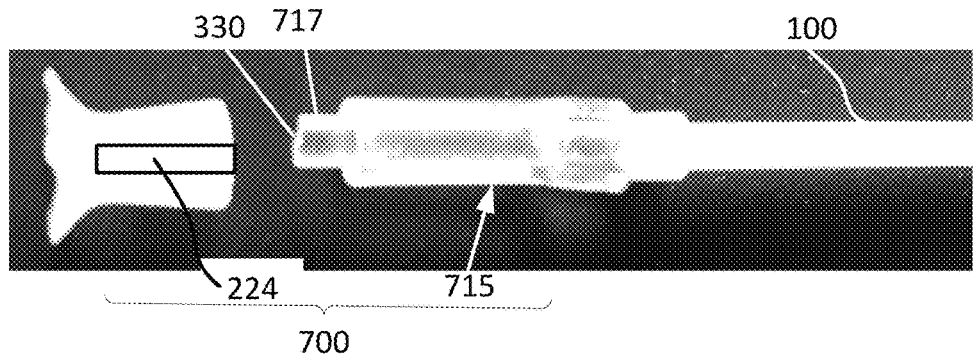
FIG. 21 is a photograph of an embodiment of a suction cup having a safety mechanism with an incorporated guide, according to the subject invention.
Figure 22:
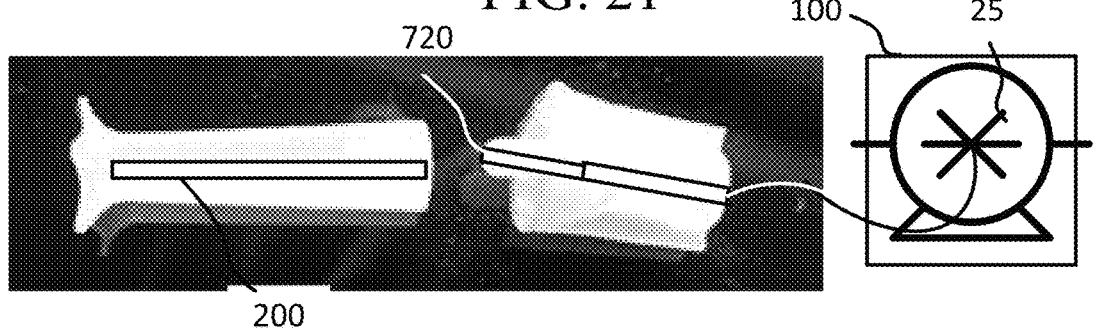
FIG. 22 illustrates an embodiment of an over-sleeve with a safety mechanism operably connected to a pump of a lens manipulator.

In one embodiment, the plug 715 has a nipple 717 that can be friction fit into the distal end opening 210. The friction fit can be sufficient to hold the over-sleeve 200 in place regardless of the vertical or horizontal orientation. FIGS. 20 and 21 illustrate non-limiting examples of a safety mechanism 700 having plugs 715 with nipples 717 that can be fit into the distal end opening 210 of a lumen 224.

In another embodiment, the plug 715 has a skirt 330 around the proximal end 10 into which the distal end 20 of the stem 210 can be inserted. Thus, the skirt can surround the distal end of the stem 210 of the over-sleeve 200. The skirt can form a friction fit with the plug to hold the over-sleeve in place regardless of the vertical or horizontal orientation. FIG. 20 illustrates a non-limiting embodiment of a plug 715 having a skirt 730 that can surround the distal end of a stem.

The plug can be held manually or attached to a lens manipulator 100. The suction cup of an over-sleeve can be used to form a vacuum with a contact lens. As an axial load is applied to the contact lens with the over-sleeve, the friction fit holds the plug and the over-sleeve together as the contact lens is removed. If the axial load exceeds a pre-determined threshold, whereby the contact lens will not release from the eye, the force of the friction fit can be overcome causing the plug to disengage from the channel. This allows air or other gases to move into the channel and the suction cup, thereby releasing the vacuum force between the contact lens and the suction cup.

A lens manipulator 100 can include a pump 25 for generating a vacuum between the suction cup and a contact lens. As described above, embodiments of an over-sleeve 200 can have a lumen 224 that can be operatively connected to a pump, as illustrated, for example, in FIG. 22. An over-sleeve of the subject invention that employs a safety mechanism 700 can also be utilized with a lens manipulator. In one embodiment, the plug can have a co-lumen 720. When the over-sleeve is friction fit with the plug, as described above, the lumen 224 and the co-lumen 720 can be integral or continuous with each other. When the over-sleeve and safety mechanism are utilized with a lens manipulator 100, the lumen 224 can be operatively connected to the co-lumen 220, which can be operatively connected to a pump, as demonstrated in FIG. 22. When the suction cup is applied to the contact lens, the pump can generate a vacuum by pulling air through the lumen and the co-lumen.

Advantageously, the safety mechanism can also operate with a lens manipulator 100. As described above, if the axial load applied to remove a contact lens exceeds a certain, pre-determined threshold, the plug can disengage from the stem, separating the lumen from the co-lumen, thereby breaking the vacuum formed by the pump. Even if the pump is configured to emit air into the suction cup to break a vacuum seal, it can be advantageous for the over-sleeve to be removable from the plug, so that the contact lens can be further manipulated away from the lens manipulator.

Lens manipulators 100 can have visual indicators 330 that assist in guiding and aligning the eye with the suction cup during handling of a contact lens. By looking at the indicator 330 as the suction cup approaches the eye, the contact lens and/or suction cup can be centered on the cornea. Alternatively, looking away from or sideways to the indicator 330 can facilitate an eccentric contact lens removal, described above.

In one embodiment, the indicator is centered in the concave surface 7 of a contact lens. In a further embodiment, the indicator is a light or light-guide directed through a lumen 224, such that the light can be seen through the pore 205 of the lumen. For example, a light generating mechanism can be placed at the distal end of the lumen. A light generating mechanism can be an electrical apparatus that has a light bulb. Alternatively, a light generating mechanism can be a fiber optic material capable of transmitting light into the lumen.

In a particular embodiment, a plug 315 can be a light generating mechanism, such that the plug has a dual function as part of a safety mechanism 700 and as an indicator 330. In one embodiment, shown, for example, in FIG. 21, a plug can be formed of a light transmitting material. When the plug is coupled to the stem, the light of the plug is transmitted into the lumen 224. The plug can function as described above. In a further embodiment, the plug can be operatively connected to a lens manipulator 100 that generates the light transmitted through the plug, which is shown by way of example, in FIG. 21.

Placement and removal of a contact lens from the eye can be difficult for some patients. Rigid Gas Permeable lenses and hybrid lenses can provide a particular challenge because of their size and unique hard/soft configurations. The application of medicaments or other substances to the eye can also be challenging. The embodiments of the subject invention provide devices that make the insertion and removal of these types of lenses and the application of substances to the eye easier, safer, and minimize the possibility of damage to the eye. A lens manipulator of the subject invention can be configured with sufficient suction force to hold a contact lens in place, on the suction cup, during insertion and still release from the contact lens after insertion. A lens manipulator of the subject invention can also include a safety release feature that releases the suction cup from the contact lens if the contact lens cannot be removed from the eye or if the suction cup cannot be removed from the contact lens.

All patents, patent applications, provisional applications, and other publications referred to or cited herein are incorporated by reference in their entirety, including all figures and tables, to the extent they are not inconsistent with the explicit teachings of this specification. Additionally, the entire contents of the references cited within the references cited herein are also entirely incorporated by reference.

The examples and embodiments described herein are for illustrative purposes only and that various modifications or changes in light thereof will be suggested to persons skilled in the art and are to be included within the spirit and purview of this application.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A lens manipulator, adapted for handling a contact lens, comprising an over-sleeve with a suction cup comprising one or more discontinuities on a peripheral edge and a lumen therethrough, where the lumen is contiguous with the suction cup, the suction cup having a suction force that is adjustable by positioning an adjustment rod in the lumen to change a volume between the suction cup and the adjustment rod.

2. The lens manipulator according to claim 1, further comprising a cuff around the over-sleeve.

3. The lens manipulator according to claim 1, wherein the position of the adjustment rod in the lumen determines a suction force that is released when a maximum pull force is exerted against the suction cup.

4. The lens manipulator according to claim 3, wherein the over-sleeve is removed from the adjustment rod when the maximum pull force is exceeded thereby eliminating suction force under the suction cup.

5. The lens manipulator according to claim 1, wherein the discontinuities are adapted to support at least a contact lens on the peripheral edge and inhibit formation of suction between the contact lens and the suction cup.

6. The lens manipulator according to claim 5, wherein the application of force against the one or more discontinuities cause the discontinuities to deflect, thereby exposing a leading edge adapted to make contact and form suction with the contact lens.

7. A lens manipulator comprising:
an over-sleeve having a suction cup at a proximal end, adapted to engage with a contact lens, and a stem at a distal end, with a lumen therethrough that forms a pore in the suction cup and a rod opening in the stem;
an adjustment rod having a proximal end moveably inserted through the rod opening and into the lumen, such that the distance that the adjustment rod is inserted into the lumen controls the suction force under the suction cup; and
a cuff that at least partially surrounds the stem of the over-sleeve.

8. The lens manipulator according to claim 7, further comprising a detent on the adjustment rod that engages with the lumen.

9. The lens manipulator according to claim 7, wherein the suction force formed by the suction cup with a contact lens is adjustable between 20 grams and 195 grams.

10. The lens manipulator according to claim 9, wherein the suction force formed by the suction cup with a contact lens is adjustable between 50 grams and approximately 190 grams.

11. The lens manipulator according to claim 10, wherein the suction force formed by the suction cup with a contact lens is 115 grams.

12. The lens manipulator according to claim 7, further comprising a tensioning sleeve with a bore in which the adjustment rod can be moveably disposed, such that the tensioning sleeve is usable to adjust the length of adjustment rod that protrudes from the tensioning sleeve, thereby controlling the distance the adjustment rod is inserted into the lumen.

13. The lens manipulator according to claim 7, wherein the proximal end of the adjustment rod inserted into the rod opening is angled relative to a longitudinal length of the lens manipulator.

14. The lens manipulator according to claim 13, wherein the angle of the adjustment rod is approximately 90° relative to the longitudinal length of the lens manipulator.

15. A method for handling a contact lens comprising:
positioning a contact lens on a lens manipulator, according to claim 7,
adjusting the adjustment rod in the lumen, such that minimal or no suction force is formed between the contact lens and the suction cup,
advancing the suction cup with the contact lens thereon into proximity with an eye until the contact lens transfers to the surface of the eye, and
moving the lens manipulator away from the eye to leave the contact lens on the eye.

16. The method according to claim 15, further comprising:
advancing the suction cup into proximity with the contact lens on the eye,
pushing the suction cup against the contact lens to form suction between the contact lens and the suction cup, and
exerting a pulling force directed away from the eye until the contact lens disengages from the eye.

17. The method according to claim 16, further comprising re-adjusting the distance that the adjustment rod is inserted into the lumen to achieve a maximum pull force.

18. The method according to claim 17, wherein exceeding the maximum pull force, when exerting a pulling force directed away from the eye, will cause the adjustment rod to be removed from the lumen, thereby eliminating the suction force between the contact lens and the suction cup.

19. The method according to claim 16, further comprising one or more discontinuities on or around at least a portion of a peripheral edge of the suction cup.

20. The method according to claim 19, wherein the discontinuities are adapted to support at least a contact lens on the peripheral edge and inhibit formation of suction between the contact lens and the suction cup.

21. The method according to claim 20, wherein the application of force against the one or more discontinuities causes the discontinuities to deflect, thereby exposing a leading edge adapted to make contact and form suction with the contact lens.

22. A method for extracting a contact lens from the surface of an eye comprising:
obtaining a lens manipulator according to claim 7,
adjusting the distance that the adjustment rod is inserted into the lumen to achieve a maximum pull force between the suction cup and the contact lens,
advancing the suction cup nto proximity with the eye until the suction cup forms a suction force with a contact lens thereon, and
moving the lens manipulator away from the eye with the contact lens engaged with the suction cup to emove the contact lens from the eye.

23. The method according to claim 22, wherein exceeding the maximum pull force will cause the adjustment rod to be removed from the lumen, thereby eliminating the suction force and wherein the method further comprises moving the lens manipulator away from the eye until the maximum pull force is exceeded, so as to eliminate the suction force between the suction cup and the contact lens.

24. The lens manipulator according to claim 7, further comprising one or more discontinuities, in a peripheral edge of the suction cup, including at least one of holes, fenestrations, openings and vents, lobes, petals, fingers, teeth, serrations, and indentations.

* * * * *